(12) United States Patent
Niimi et al.

(10) Patent No.: US 11,541,594 B2
(45) Date of Patent: Jan. 3, 2023

(54) ULTRASONIC PROPAGATION MEMBER AND METHOD FOR PRODUCING SAME

(71) Applicant: RICOH COMPANY, LTD., Tokyo (JP)

(72) Inventors: Tatsuya Niimi, Kanagawa (JP); Takashi Matsumura, Kanagawa (JP); Takuya Saito, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 126 days.

(21) Appl. No.: 16/601,846

(22) Filed: Oct. 15, 2019

(65) Prior Publication Data

US 2020/0138407 A1 May 7, 2020

(30) Foreign Application Priority Data

Nov. 6, 2018 (JP) .............................. JP2018-208757
Nov. 6, 2018 (JP) .............................. JP2018-208761

(51) Int. Cl.
*B29C 64/106* (2017.01)
*C08K 3/34* (2006.01)
*C08L 33/26* (2006.01)
*A61B 8/00* (2006.01)

(52) U.S. Cl.
CPC ............ *B29C 64/106* (2017.08); *C08K 3/346* (2013.01); *C08L 33/26* (2013.01); *A61B 8/4281* (2013.01)

(58) Field of Classification Search
CPC .... A61B 8/4281; B29C 64/106; G10K 11/02; C08K 3/346; C08L 33/26
See application file for complete search history.

(56) References Cited

U.S. PATENT DOCUMENTS

| | | | | |
|---|---|---|---|---|
| 5,505,205 | A * | 4/1996 | Solomon | G10K 11/02 600/459 |
| 5,782,767 | A * | 7/1998 | Pretlow, III | A61B 8/4281 600/443 |
| 2008/0281237 | A1* | 11/2008 | Slayton | G10K 11/30 601/2 |
| 2011/0313293 | A1* | 12/2011 | Lindekugel | A61B 8/44 600/461 |
| 2012/0238859 | A1* | 9/2012 | Tokita | A61B 8/0825 600/407 |

(Continued)

FOREIGN PATENT DOCUMENTS

| | | |
|---|---|---|
| JP | 03-272750 | 12/1991 |
| JP | H04-332543 | 11/1992 |

(Continued)

OTHER PUBLICATIONS

U.S. Appl. No. 16/546,818, filed Aug. 21, 2019.
(Continued)

*Primary Examiner* — Catherine B Kuhlman
*Assistant Examiner* — Sean A Frith
(74) *Attorney, Agent, or Firm* — Grüneberg and Myers, PLLC

(57) ABSTRACT

Provided is an ultrasonic propagation member used in contact with a test target, wherein a surface of the ultrasonic propagation member contacting the test target has a shape conforming to a surface of the test target, or an ultrasonic propagation member having at least two surfaces, wherein hardness of one surface and hardness of another surface are different.

20 Claims, 10 Drawing Sheets

(56) References Cited

U.S. PATENT DOCUMENTS

| | | | |
|---|---|---|---|
| 2013/0041260 A1* | 2/2013 | Schmidt | A61B 8/406 600/442 |
| 2014/0094702 A1* | 4/2014 | Kim | A61B 8/0858 600/438 |
| 2016/0115297 A1* | 4/2016 | Norikane | B29C 64/129 428/218 |
| 2016/0275818 A1 | 9/2016 | Norikane et al. | |
| 2017/0008228 A1* | 1/2017 | Iwata | B29C 64/40 |
| 2017/0022348 A1 | 1/2017 | Iwata et al. | |
| 2017/0128042 A1* | 5/2017 | Desai | A61B 8/4422 |
| 2017/0239886 A1 | 8/2017 | Norikane | |
| 2017/0270831 A1 | 9/2017 | Norikane et al. | |
| 2017/0325692 A1* | 11/2017 | Nishihara | A61B 5/0095 |
| 2017/0328794 A1* | 11/2017 | McLaughlin | G01L 1/241 |
| 2017/0369607 A1 | 12/2017 | Iwata et al. | |
| 2018/0061279 A1 | 3/2018 | Niimi et al. | |
| 2018/0126651 A1 | 5/2018 | Matsumura et al. | |
| 2018/0301065 A1 | 10/2018 | Norikane et al. | |
| 2018/0312664 A1 | 11/2018 | Norikane et al. | |
| 2018/0345036 A1 | 12/2018 | Niimi et al. | |
| 2018/0345574 A1 | 12/2018 | Matsumura et al. | |
| 2019/0010259 A1 | 1/2019 | Iwata et al. | |
| 2019/0060675 A1* | 2/2019 | Krone | A61N 7/00 |
| 2019/0104823 A1* | 4/2019 | Giron | B29C 33/3842 |
| 2019/0175151 A1 | 6/2019 | Niimi et al. | |
| 2019/0286103 A1* | 9/2019 | Haida | G05B 19/4099 |

FOREIGN PATENT DOCUMENTS

| | | |
|---|---|---|
| JP | 2013-535301 | 9/2013 |
| JP | 2015-138192 | 7/2015 |
| JP | 2018-153936 | 10/2018 |

OTHER PUBLICATIONS

U.S. Appl. No. 16/366,339, filed Mar. 27, 2019.
Japanese Office Action dated Aug. 23, 2022, in Japanese Application No. 2018-208757, with English translation, 5 pages.
Japanese Office Action dated Aug. 23, 2022, in Japanese Application No. 2018-208761, with English translation, 5 pages.

\* cited by examiner

Dispersed in water

ULTRASONIC PROPAGATION MEMBER AND METHOD FOR PRODUCING SAME

CROSS-REFERENCE TO RELATED APPLICATIONS

The present application claims priority under 35 U.S.C. § 119 to Japanese Patent Application No. 2018-208761 filed Nov. 6, 2018, and Japanese Patent Application No. 2018-208757 filed Nov. 6, 2018. The contents of which are incorporated herein by reference in their entirety.

BACKGROUND OF THE INVENTION

Field of the Invention

The present disclosure relates to an ultrasonic propagation member and a method for producing an ultrasonic propagation member.

Description of the Related Art

Ultrasonography is performed by bringing an ultrasonic receiver into contact with the surface of a human body and receiving ultrasonic waves emitted from inside the human body. Here, if the ultrasonic receiver is simply brought into contact with the surface of the human body, the air between the ultrasonic receiver and the surface of the human body may become an obstacle of ultrasonic propagation, to hinder the diagnosis.

In order to prevent this trouble, the diagnosis is performed by placing a gelatinous substance (jelly) having a close acoustic impedance to the human body between the ultrasonic receiver and the surface of the human body. However, gelatinous substances are inconvenient to handle, and are typically stored in, for example, tubes and directly applied to the surface of the human body when used. Gelatinous substances are very sticky and give a feeling of discomfort to the examinee. There is another problem that gelatinous substances are difficult to wipe off after used and extremely troublesome.

In order to overcome these problems, there has been proposed an ultrasonic gel sheet containing a polymeric water-containing gel (for example, see Japanese Unexamined Patent Application Publication No. 03-272750).

SUMMARY OF THE INVENTION

According to one aspect of the present disclosure, an ultrasonic propagation member is an ultrasonic propagation member used in contact with a test target, and a surface of the ultrasonic propagation member contacting the test target has a shape conforming to the surface of the test target.

DESCRIPTION OF THE EMBODIMENTS

First Embodiment (Ultrasonic Propagation Member)

An ultrasonic propagation member of the present disclosure is an ultrasonic propagation member used in contact with a test target, and a surface of the ultrasonic propagation member contacting the test target has a shape conforming to the surface of the test target.

The present disclosure has an object to provide an ultrasonic propagation member that can be brought into close adhesion with the surface of a test target without gaps and can make post handling after testing unnecessary or simple.

The present disclosure can provide an ultrasonic propagation member that can be brought into close adhesion with the surface of a test target without gaps and can make post handling after testing unnecessary or simple.

Figure 1:
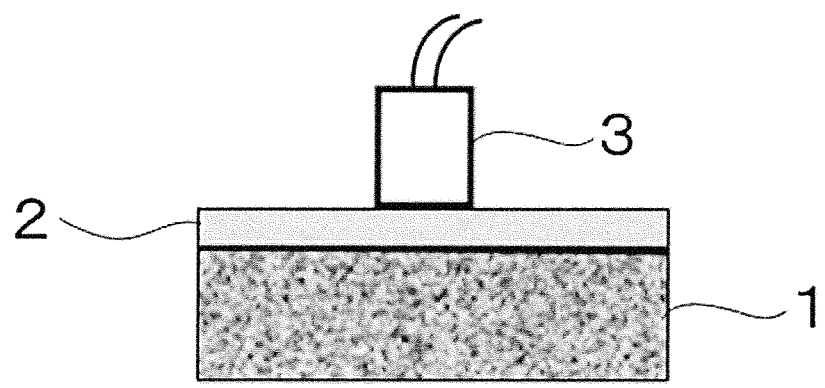
FIG. 1 is a schematic view illustrating a state in which ultrasonography is performed in an existing manner.

When using existing ultrasonic propagation members for ultrasonography, fluidic gel (jelly) is put out on the surface of the skin of the examinee and applied over the surface of the skin by being drawn by an ultrasonic receiver when used. As illustrated in FIG. 1, the diagnosis is performed by bringing the ultrasonic receiver 3 into contact with the surface of the skin 1 of the examinee having the fluidic gel 2 applied, such that the fluidic gel 2 serves to eliminate air (gaps) from between both. In the case of using such fluidic gel, there is a need for applying the fluidic gel every time examinees are changed or every time parts to be diagnosed are changed. Further, there is a drawback that such fluidic gel has a sticky touch, which often makes the examinee feel uncomfortable and is very bothersome because an operation for wiping off the fluidic gel from the human body is needed.

Figure 2:
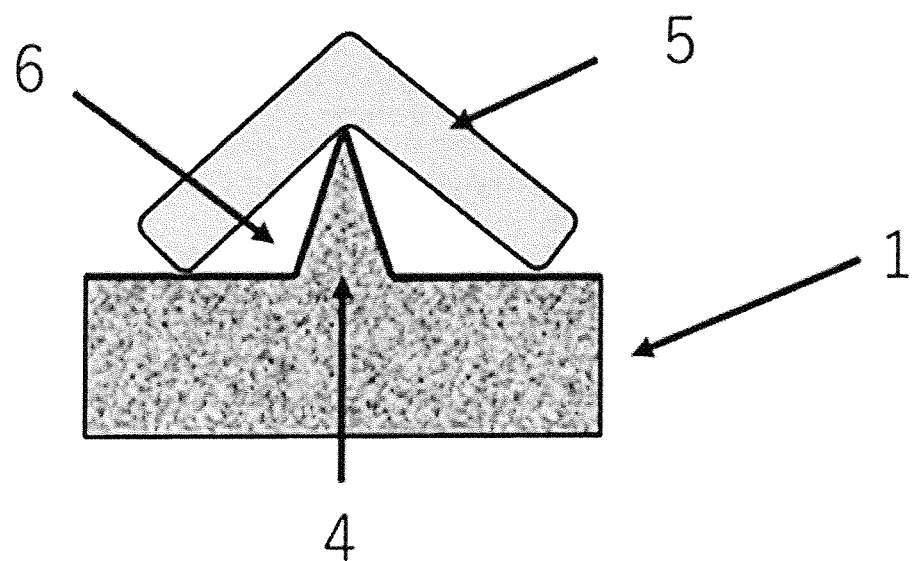
FIG. 2 is a schematic view of a case where a gel sheet having a planar structure is brought into contact with the surface of a human body.

Further, according to existing techniques, a modified embodiment of the fluidic gel 2 illustrated in FIG. 1, i.e., a gel sheet 5 illustrated in FIG. 2 is known. In this case, the diagnosis is performed by placing the gel sheet 5 on the surface of the skin 1 of the examinee and pressing the gel sheet 5 by an ultrasonic receiver to make the gel sheet 5 closely adhere to the surface of the skin.

Because the gel sheet 5 has a flat plate shape produced using a die, it is difficult to bring the gel sheet 5 into complete close adhesion with the surface of the skin 1 of the examinee without a gap. Therefore, there is a drawback that gaps 6 tend to occur and bubbles tend to mix when there is a convex portion 4 over the surface of the skin as illustrated in FIG. 2. In order to make it harder for bubbles to mix, there is a need for strongly pressing the ultrasonic receiver on the human body. This may give a pain to the examinee depending on the body part.

The ultrasonic propagation member of the present disclosure has been made in view of the findings described above, and is an ultrasonic propagation member used in contact with a test target, wherein a surface of the ultrasonic propagation member contacting the test target has a shape conforming to the surface of the test target. This saves the examinee, who is the test target, from a feeling of discomfort, and makes post handling after testing unnecessary. Further, in terms of operability, the ultrasonic propagation member has an excellent close adhesiveness and makes ultrasonographic diagnoses smooth.

The test target is not particularly limited and may be appropriately selected depending on the intended purpose. Examples of the test target include an examinee of an ultrasonographic diagnosis.

Figure 3:
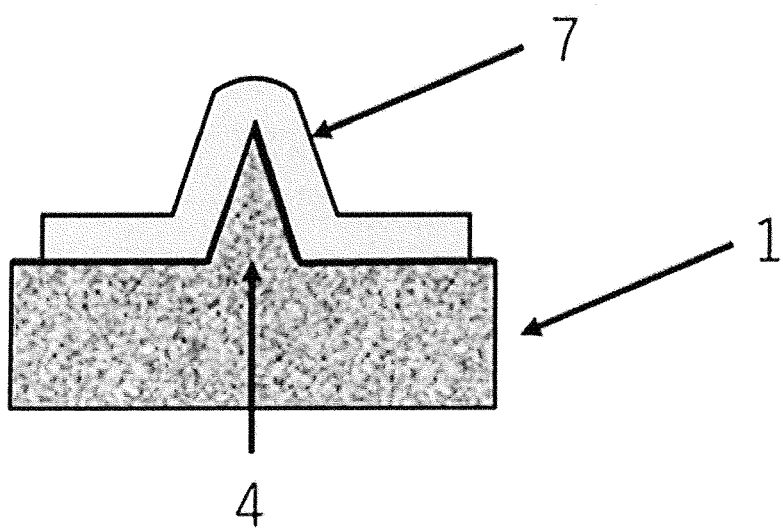
FIG. 3 is a view of a case where an ultrasonic propagation member having a structure conforming to the shape of the surface of a human body is brought into contact with the surface of a human body.

The ultrasonic propagation member of the present disclosure has a shape conforming to the surface of the human body of the examinee, who is the test target, based on the personal data of the examinee. As a result, the ultrasonic propagation member 7 can fit the skin of the examinee without gaps even when there is a convex portion 4 over the surface of the human body as illustrated in FIG. 3.

When it is said that the surface of the ultrasonic propagation member contacting the test target has a shape conforming to the surface of the test target, it is meant that the surface of the ultrasonic propagation member has a certain shape that is convex or concave with respect to a concave portion or a convex portion present over the surface of the test target, and there is no need for bringing the ultrasonic propagation member into close adhesion with the concave portion or the convex portion (or deforming the ultrasonic propagation member to conform to the concave portion or the convex portion) of the test target by strongly pressing the ultrasonic propagation member against the concave portion or the convex portion of the test target. For example, for the ultrasonography purpose, an ultrasonic propagation member originally having a shape matching a concave portion or a convex portion of the part, to be tested, of the human body of the examinee needs only to be positioned in alignment with the part to be tested, and can follow slight fluctuations during the diagnosis. Therefore, such an ultrasonic propagation member can contribute to an accurate, quick ultrasonographic diagnosis.

The ultrasonic propagation member of the present disclosure contains water, a polymer, and a mineral, preferably contains an organic solvent, and further contains other components as needed.

It is preferable that the ultrasonic propagation member be formed of a hydrogel that is formed by a solvent being contained in a three-dimensional network structure formed by the mineral, which is dispersed in an organic solvent, being cross-linked and combined with the polymer, which is produced from polymerization of a polymerizable monomer.

—Polymer—

Examples of the polymer include polymers containing an amide group, an amino group, a hydroxyl group, a tetramethyl ammonium group, a silanol group, and an epoxy group. The polymer is preferably water-soluble.

The polymer may be a homopolymer or a heteropolymer (copolymer), may be modified, may have a known functional group introduced, or may be in the form of a salt. The polymer is preferably a homopolymer.

In the present disclosure, water-solubility of the polymer means that, for example, when 1 g of the polymer is mixed and stirred in 100 g of water having a temperature of 30 degrees C., 90% by mass or greater of the polymer dissolves.

The polymer is obtained by polymerizing a polymerizable monomer. The polymerizable monomer will be described in a method for producing an ultrasonic propagation member described below.

—Water—

As the water, for example, pure water such as ion-exchanged water, ultrafiltrated water, reverse osmotic water, and distilled water or ultrapure water can be used.

The content of the water is preferably 70% by mass or greater but 95% by mass or less and more preferably 75% by mass or greater but 90% by mass or less relative to the total amount of the ultrasonic propagation member in terms of the ultrasonic propagation performance.

Any other component such as an organic solvent may be dissolved or dispersed in the water with a view to, for example, imparting a moisture retaining property, imparting an antimicrobial activity, imparting conductivity, and adjusting hardness.

—Mineral—

The mineral is not particularly limited and may be appropriately selected depending on the intended purpose. Examples of the mineral include a water-swellable layered clay mineral.

Figure 4:
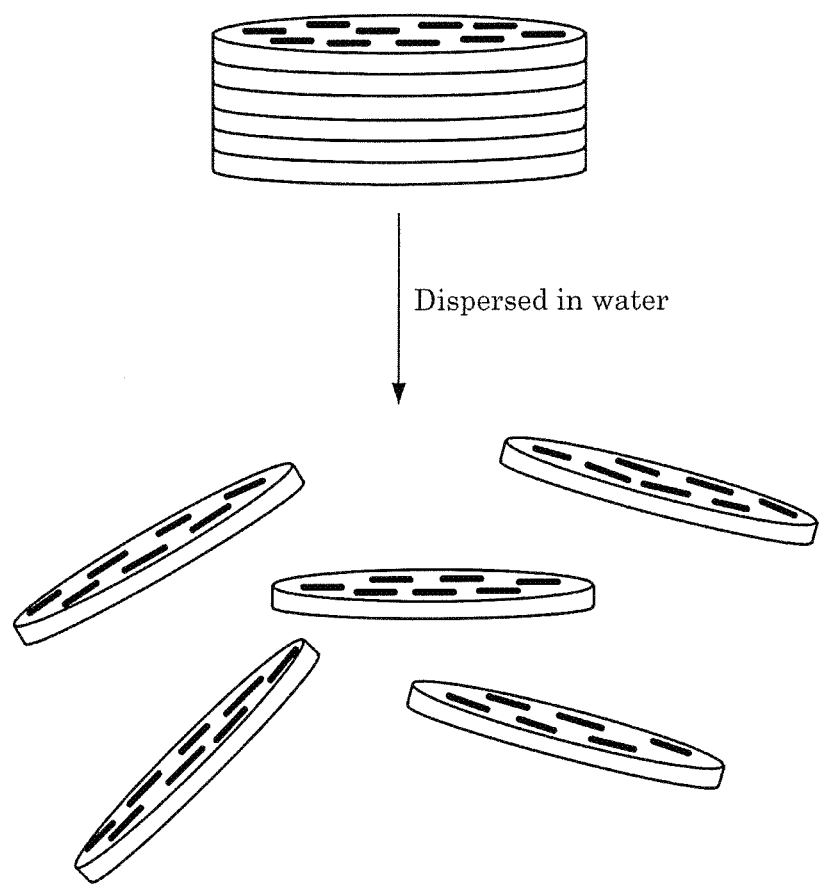
FIG. 4 is an exemplary view illustrating a water-swellable layered clay mineral serving as a mineral, and a state of the water-swellable layered clay mineral being dispersed in water.

The water-swellable layered clay mineral has a state wherein two-dimensional discoid crystals including a unit lattice in the crystals are stacked as illustrated in the upper section of FIG. 4 illustrating a state of single layers being dispersed in water. When the water-swellable layered clay mineral is dispersed in water, the crystals are separated into single-layer forms to become discoid crystals as illustrated in the lower section of FIG. 4.

Examples of the water-swellable layered clay mineral include water-swellable smectite and water-swellable mica. More specific examples of the water-swellable layered clay mineral include water-swellable hectorite containing sodium as an interlayer ion, water-swellable montmorillonite, water-swellable saponite, and water-swellable synthetic mica. One of these water-swellable layered clay minerals may be used alone or two or more of these water-swellable layered clay minerals may be used in combination. Among these water-swellable layered clay minerals, water-swellable hectorite is preferable because an ultrasonic propagation member having a high elasticity can be obtained.

The water-swellable hectorite may be an appropriately synthesized product or a commercially available product. Examples of the commercially available product include synthetic hectorite (LAPONITE XLG, available from Rock Wood), SWN (available from Coop Chemical Ltd.), and fluorinated hectorite SWF (available from Coop Chemical Ltd.). Among these commercially available products, synthetic hectorite is preferable in terms of the elastic modulus of the ultrasonic propagation member.

Water-swellability means that a layered clay mineral is dispersed in water when water molecules are inserted between layers of the layered clay mineral as illustrated in FIG. 4.

The content of the mineral is preferably 1% by mass or greater but 40% by mass or less and more preferably 1% by mass or greater but 25% by mass or less relative to the total amount of the ultrasonic propagation member in terms of the elastic modulus and hardness of the ultrasonic propagation member.

—Organic Solvent—

The organic solvent is contained in order to increase the moisture retaining property of the ultrasonic propagation member.

The organic solvent is not particularly limited and may be appropriately selected depending on the intended purpose. Examples of the organic solvent include: alkyl alcohols containing from 1 through 4 carbon atoms, such as methyl alcohol, ethyl alcohol, n-propyl alcohol, isopropyl alcohol, n-butyl alcohol, sec-butyl alcohol, and tert-butyl alcohol; amides such as dimethyl formamide and dimethyl acetamide; ketones or ketone alcohols such as acetone, methyl ethyl ketone, and diacetone alcohol; ethers such as tetrahydrofuran and dioxane; polyvalent alcohols such as ethylene glycol, propylene glycol, 1,2-propanediol, 1,2-butanediol, 1,3-butanediol, 1,4-butanediol, diethylene glycol, triethylene glycol, 1,2,6-hexanetriol, thioglycol, hexylene glycol, and glycerin; polyalkylene glycols such as polyethylene glycol and polypropylene glycol; lower alcohol ethers of polyvalent alcohols, such as ethylene glycol monomethyl (or ethyl) ether, diethylene glycol methyl (or ethyl) ether, and triethylene glycol monomethyl (or ethyl) ether; alkanol amines such as monoethanol amine, diethanol amine, and triethanol amine; N-methyl-2-pyrrolidone; 2-pyrrolidone; and 1,3-dimethyl-2-imidazolidinone. One of these organic solvents may be used alone or two or more of these organic solvents may be used in combination. Among these organic solvents, polyvalent alcohols are preferable and glycerin and propylene glycol are more preferable in terms of a moisture retaining property.

The content of the organic solvent is preferably 10% by mass or greater but 50% by mass or less relative to the total amount of the ultrasonic propagation member. When the content of the organic solvent is 10% by mass or greater, an effect of preventing drying can be sufficiently obtained. When the content of the organic solvent is 50% by mass or less, the layered clay mineral is uniformly dispersed.

When the content of the organic solvent is 10% by mass or greater but 50% by mass or less, a favorable functionality as an ultrasonic propagation member can be obtained with a small difference from the body composition.

—Other Components—

The other components are not particularly limited and may be appropriately selected depending on the intended purpose. Examples of the other components include a phosphonic acid compound such as 1-hydroxyethane-1,1-diphosphonic acid, a stabilizing agent, a surface treating agent, a polymerization initiator, a colorant, a viscosity modifier, a tackifier, an antioxidant, an age resistor, a cross-linking promoter, an ultraviolet absorber, a plasticizer, an antiseptic, and a dispersant.

<Coating Film>

It is effective to provide a coating film over the surface of the ultrasonic propagation member for the following three purposes.

(1) To maintain the shape of the ultrasonic propagation member (2) To improve the storage stability (drought resistance and antiseptic property) of the ultrasonic propagation member (3) To improve the appearance of the ultrasonic propagation member In order to maintain the shape of the ultrasonic propagation member, it is preferable to impart an elastic force to the coating film for preventing collapse of the ultrasonic propagation member due to the deadweight. It is preferable that a difference in hardness (Young's modulus) of the ultrasonic propagation member due to presence and absence of the coating film be 0.01 MPa or greater.

The material forming the coating film is not particularly limited and may be appropriately selected depending on the intended purpose. Examples of the material include polyester, polyolefin, polyethylene terephthalate, PPS, polypropylene, polyvinyl alcohol (PVA), polyethylene, polyvinyl chloride, cellophane, acetate, polystyrene, polycarbonate, nylon, polyimide, fluororesins, and paraffin waxes. One of these materials may be used alone or two or more of these materials may be used in combination.

As the material forming the coating film, a commercially available product may be used. Examples of the commercially available product include PLASTICOAT #100 (available from Daikyo Chemical Co., Ltd.) and POVAL 205 (available from Kuraray Co., Ltd.).

The film thickness of the coating film is not particularly limited, may be appropriately selected depending on the intended purpose, and is preferably 100 micrometers or less and more preferably 10 micrometers or greater but 50 micrometers or less. When the film thickness of the coating film is 100 micrometers or less, there is an advantage that the texture of the hydrogel constituting the ultrasonic propagation member can be maintained.

It is possible to improve the appearance of the ultrasonic propagation member by forming the coating film over the surface of the ultrasonic propagation member. For example, when the surface of the ultrasonic propagation member has a scar or a surface roughness, the coating film can make up for the appearance. Moreover, the internal ultrasonic propagation member can be protected when the coating film over the surface serves as a sacrificial layer.

Furthermore, because the surface of the ultrasonic propagation member does not accept writing such as marking, the coating film formed over the surface of the ultrasonic propagation member can add to the functionality as the ultrasonic propagation member, allowing, for example, the procedure of an ultrasonographic diagnosis, the part to be measured, and the name of the examinee to be written.

The method for forming the coating film is not particularly limited and may be appropriately selected depending on the intended purpose. Examples of the method include a method of dissolving the material for forming the coating film in a solvent and coating the resultant over the surface of the ultrasonic propagation member. Examples of the coating method include a brush, spray, and dip coating.

Examples of the method also include a method of using a heat-shrinkable film as the material for forming the coating film and laminating the heat-shrinkable film over the surface of the ultrasonic propagation member.

Moreover, it is also possible to dissolve the material for forming the coating film in a solvent and simultaneously form the coating film when producing the ultrasonic propagation member using a three-dimensional printer and a liquid material for producing an ultrasonic propagation member.

In any case, what matters is close adhesiveness with skin. Therefore, what matters is to form a coating film that would not spoil the shape of the surface of the ultrasonic propagation member produced based on three-dimensional data of a body surface, to be ultrasonographically diagnosed, of an individual examinee.

In order to improve the storage stability of the ultrasonic propagation member, there is a need for improving the drought resistance and the antiseptic property.

In order to improve the drought resistance, it is effective to suppress the water vapor permeability and the oxygen permeability of the coating film. Specifically, the water vapor permeability (JIS K7129) of the ultrasonic propagation member is preferably 500 g/m$^2$·day or lower. The oxygen permeability (JIS Z1702) of the ultrasonic propagation member is preferably 100,000 cc/m$^2$/hr/atm or lower.

In order to improve the antiseptic property, it is preferable to add an antiseptic in the coating film. The antiseptic is not particularly limited and may be appropriately selected depending on the intended purpose. Examples of the antiseptic include dehydroacetate, sorbate, benzoate, pentachlorophenol sodium, 2-pyridinethiol-1-oxide sodium, 2,4-dimethyl-6-acetoxy-m-dioxane, and 1,2-benzthiazolin-3-one.

For example, the shape, size, structure, and properties of the ultrasonic propagation member are not particularly limited and may be appropriately selected depending on the intended purpose.

The hydrogel contained in the ultrasonic propagation member of the present disclosure is formed of a polymer, water, and a mineral, and hence has a close composition to a human body in the first place. Therefore, the acoustic impedance of the hydrogel is close to the acoustic impedance value of a human body. Hence, when the hydrogel can be placed over the surface of a human body with a good close adhesiveness between both, ultrasonic waves emitted from inside the body can be transmitted to an ultrasonic receiver without being reflected (attenuated).

As described above, a structure having a sufficient flexibility for close adhesion at a side facing the surface of a human body can be ensured a sufficient close adhesiveness. Hence, the ultrasonic propagation member containing a hydrogel satisfies all properties and features that are needed as an ultrasonic propagation member. A hydrogel can be raised as one of the best materials for constituting the ultrasonic propagation member.

—Hardness (Young's Modulus)—

The ultrasonic propagation member of the present disclosure needs to have an appropriate hardness in terms of handleability and close adhesiveness with a human body. It is difficult to quantify the hardness of such a material (member) as having considerable flexibility and fracture toughness like the ultrasonic propagation member of the present disclosure. However, the hardness of such a material can be defined by Young's modulus.

A Young's modulus can be measured by, for example, mechanical testing methods, resonance methods, and ultrasonic pulse methods. Mechanical testing methods that can measure a measurand in simple manners are effective for a considerably flexible material as in the present disclosure.

The hardness of the ultrasonic propagation member of the present disclosure expressed by Young's modulus is preferably 0.5 kPa or greater but 100 kPa or less and more preferably 1 kPa or greater but 50 kPa or less.

When the Young's modulus is extremely low, the ultrasonic propagation member cannot retain shape due to the deadweight and serve the function as an ultrasonic propagation member. Conversely, when the Young's modulus is extremely high, the ultrasonic propagation member may have a poor close adhesiveness with a human body.

—Transmittance—

What matters as the ultrasonic propagation member is close adhesiveness with a human body, and it is preferable if it is possible to visually confirm the degree of contact based on, for example, presence or absence of bubbles. Hence, transmittance of the ultrasonic propagation member in the visible range (400 nm or longer but 700 nm or shorter) is preferably 70% or higher and more preferably 90% or higher.

Transmittance can be measured with, for example, a commercially available spectrophotometer.

—Ultrasonic Propagation Velocity—

The ultrasonic propagation member needs to closely adhere to a human body and propagate a received signal to a sensor. Because the composition of a human body is mostly formed of water, it is preferable that the ultrasonic propagation velocity in the ultrasonic propagation member be close to the ultrasonic propagation velocity in water in order for an ultrasonic wave signal to be efficiently received.

Ultrasonic propagation velocity has a temperature dependency, and is about 1,500 m/sec in water at room temperature (25 degrees C.). The ultrasonic propagation member of the present disclosure is a hydrogel mainly formed of water. The ultrasonic propagation velocity in the ultrasonic propagation member may become higher depending on the composition of the ultrasonic propagation member.

It is not preferable if a difference from the ultrasonic propagation velocity in a human body (water) is extremely large, because the detector may fail to focus and produce a poor image resolution. Therefore, it is preferable that the ultrasonic propagation velocity in the ultrasonic propagation member be within ±5% from the ultrasonic propagation velocity in water measured under the same conditions.

The ultrasonic propagation velocity can be measured according to a method described in, for example, JIS Z 2353.

(Method for Producing Ultrasonic Propagation Member)

A method for producing an ultrasonic propagation member of the present disclosure produces the ultrasonic propagation member using a liquid material for producing an ultrasonic propagation member, the liquid material containing water, a mineral, and a polymerizable monomer.

<Liquid Material for Producing Ultrasonic Propagation Member>

The liquid material for producing an ultrasonic propagation member contains water, a mineral, and a polymerizable monomer, preferably contains an organic solvent, and further contains other components as needed.

The water, the mineral, the organic solvent, and the other components may be the same as the materials used in the ultrasonic propagation member described above.

—Polymerizable Monomer—

The polymerizable monomer is a compound that contains one or more unsaturated carbon-carbon bond. Examples of the polymerizable monomer include monofunctional monomers and multifunctional monomers.

Examples of the multifunctional monomers include bifunctional monomers, trifunctional monomers, and trifunctional or higher monomers.

The monofunctional monomer is a compound that contains one unsaturated carbon-carbon bond. Examples of the monofunctional monomer include acrylamide, N-substituted acrylamide derivatives, N,N-disubstituted acrylamide derivatives, N-substituted methacrylamide derivatives, N,N-disubstituted methacrylamide derivatives, and other monofunctional monomers. One of these monofunctional monomers may be used alone or two or more of these monofunctional monomers may be used in combination.

Examples of the N-substituted acrylamide derivatives, the N,N-disubstituted acrylamide derivatives, the N-substituted methacrylamide derivatives, or the N,N-disubstituted methacrylamide derivatives include N,N-dimethyl acrylamide (DMAA), and N-isopropyl acrylamide.

Examples of the other monofunctional monomers include 2-ethyl hexyl (meth)acrylate (EHA), 2-hydroxyethyl (meth)acrylate (HEA), 2-hydroxypropyl (meth)acrylate (HPA), acryloylmorpholine (ACMO), caprolactone-modified tetrahydrofurfuryl (meth)acrylate, isobornyl (meth)acrylate, 3-methoxybutyl (meth)acrylate, tetrahydrofurfuryl (meth)acrylate, lauryl (meth)acrylate, 2-phenoxyethyl (meth)acrylate, isodecyl (meth)acrylate, isooctyl (meth)acrylate, tridecyl (meth)acrylate, caprolactone (meth)acrylate, ethoxylated nonyl phenol (meth)acrylate, and urethane (meth)acrylate. One of these monofunctional monomers may be used alone or two or more of these monofunctional monomers may be used in combination.

When the monofunctional monomer is polymerized, a water-soluble organic polymer containing, for example, an amide group, an amino group, a hydroxyl group, a tetramethyl ammonium group, a silanol group, and an epoxy group is obtained.

The water-soluble organic polymer containing an amide group, an amino group, a hydroxyl group, a tetramethyl ammonium group, a silanol group, and an epoxy group is an advantageous constituent component for maintaining the strength of the ultrasonic propagation member.

The content of the monofunctional monomer is not particularly limited, may be appropriately selected depending on the intended purpose, and is preferably 1% by mass or greater but 10% by mass or less and more preferably 1% by mass or greater but 5% by mass or less relative to the total amount of the liquid material for producing an ultrasonic propagation member. When the content of the monofunctional monomer is 1% by mass or greater but 10% by mass or less, there are advantages that dispersion stability of the layered clay mineral in the liquid material for producing an ultrasonic propagation member is maintained, and that extensibility of the ultrasonic propagation member is improved. The extensibility refers to a property of the ultrasonic propagation member to extend and remain unfractured when drawn.

Examples of the bifunctional monomer include tripropylene glycol di(meth)acrylate, triethylene glycol di(meth)acrylate, tetraethylene glycol di(meth(acrylate), polypropylene glycol di(meth)acrylate, neopentyl glycol hydroxypivalic acid ester di(meth)acrylate (MANDA), hydroxypivalic acid neopentyl glycol ester di(meth)acrylate (HPNDA), 1,3-butanediol di(meth)acrylate (BGDA), 1,4-butanediol di(meth)acrylate (BUDA), 1,6-hexanediol di(meth)acrylate (HDDA), 1,9-nonanediol di(meth)acrylate, diethylene glycol di(meth)acrylate (DEGDA), neopentyl glycol di(meth)acrylate (NPGDA), tripropylene glycol di(meth)acrylate (TPGDA), caprolactone-modified hydroxypivalic acid neopentyl glycol ester di(meth)acrylate, propoxylated neopentyl glycol di(meth)acrylate, ethoxy-modified bisphenol-A di(meth)acrylate, polyethylene glycol 200 di(meth)acrylate, polyethylene glycol 400 di(meth)acrylate, and methylene bis(meth)acrylamide. One of these bifunctional monomers may be used alone or two or more of these bifunctional monomers may be used in combination.

Examples of the trifunctional monomer include trimethylolpropane tri(meth)acrylate (TMPTA), pentaerythritol tri(meth)acrylate (PETA), triallyl isocyanate, tris(2-hydroxyethyl)isocyanurate tri(meth)acrylate, ethoxylated trimethylolpropane tri(meth)acrylate, propoxylated trimethylolpropane tri(meth)acrylate, and propoxylated glyceryl tri(meth)acrylate. One of these trifunctional monomers may be used alone or two or more of these trifunctional monomers may be used in combination.

Examples of the trifunctional or higher monomer include pentaerythritol tetra(meth)acrylate, ditrimethylolpropane tetra(meth)acrylate, dipentaerythritol hydroxy penta(meth)acrylate, ethoxylated pentaerythritol tetra(meth)acrylate, penta(meth)acrylate ester, and dipentaerythritol hexa(meth)acrylate (DPHA). One of these trifunctional or higher monomers may be used alone or two or more of these trifunctional or higher monomers may be used in combination.

The content of the multifunctional monomer is preferably 0.001% by mass or greater but 1% by mass or less and more preferably 0.01% by mass or greater but 0.5% by mass or less relative to the total amount of the liquid material for producing an ultrasonic propagation member. When the content of the multifunctional monomer is 0.001% by mass or greater but 1% by mass or less, the elastic modulus and hardness of the ultrasonic propagation member to be obtained can be adjusted to appropriate ranges.

It is preferable to cure the liquid material for producing an ultrasonic propagation member using a polymerization initiator. The polymerization initiator is added in the liquid material for producing an ultrasonic propagation member when used.

—Polymerization Initiator—

Examples of the polymerization initiator include a thermal polymerization initiator and a photopolymerization initiator.

The thermal polymerization initiator is not particularly limited and may be appropriately selected depending on the intended purpose. Examples of the thermal polymerization initiator include azo-based initiators, peroxide initiators, persulfate initiators, and redox (oxidoreduction) initiators.

Examples of the azo-based initiators include VA-044, VA-46B, V-50, VA-057, VA-061, VA-067, VA-086, 2,2'-azobis(4-methoxy-2,4-dimethylvaleronitrile) (VAZO 33), 2,2'-azobis(2-amidinopropane)dihydrochloride (VAZO 50), 2,2'-azobis(2,4-dimethylvaleronitrile) (VAZO 52), 2,2'-azobis(isobutyronitrile) (VAZO 64), 2,2'-azobis-2-methylbutyronitirle (VAZO 67), and 1,1-azobis(1-cyclohexanecarbonitrile) (VAZO 88) (all available from DuPont Chemicals Company), 2,2'-azobis(2-cyclopropylpropionitrile) and 2,2'-azobis(methylisobutyrate) (V-601) (available from Wako Pure Chemical Industries, Ltd.).

Examples of the peroxide initiators include benzoyl peroxide, acetyl peroxide, lauroyl peroxide, decanoyl peroxide, dicetyl peroxydicarbonate, di(4-t-butylcyclohexyl)peroxydicarbonate (PERKADOX 16S) (available from Akzo Nobel), di(2-ethylhexyl) peroxydicarbonate, t-butyl peroxypivalate (LUPERSOL 11) (available from Elf Atochem), t-butyl peroxy-2-ethyl hexanoate (TRIGONOX 21-050) (available from Akzo Nobel), and dicumyl peroxide.

Examples of the persulfate initiators include potassium persulfate, sodium persulfate, ammonium persulfate, and sodium peroxodisulfate.

Examples of the redox (oxidoreduction) initiators include a combination of the persulfate initiator with a reducing agent such as sodium hydrogen metasulfite and sodium hydrogen sulfite, a system based on the organic peroxide and tertiary amine (for example, a system based on benzoyl peroxide and dimethyl aniline), and a system based on organic hydroperoxide and a transition metal (for example, a system based on cumene hydroperoxide and cobalt naphthenate).

As the photopolymerization initiator, an arbitrary substance that produces radicals in response to irradiation of light (an ultraviolet ray having a wavelength of from 220 nm through 400 nm) can be used.

Examples of the photopolymerization initiator include acetophenone, 2,2-diethoxyacetophenone, p-dimethyl aminoacetophenone, benzophenone, 2-chlorobenzophenone, p,p'-dichlorobenzophenone, p,p-bisdiethyl aminobenzophenone, Michler's ketone, benzyl, benzoin, benzoin methyl ether, benzoin ethyl ether, benzoin isopropyl ether, benzoin-n-propyl ether, benzoin isobutyl ether, benzoin-n-butyl ether, benzyl methyl ketal, thioxanthone, 2-chlorothioxanthone, 2-hydroxy-2-methyl-1-phenyl-1-one, 1-(4-isopropylphenyl)2-hydroxy-2-methylpropan-1-one, methylbenzoyl formate, 1-hydroxycyclohexylphenyl ketone, azobis isobutyronitrile, benzoyl peroxide, and di-tert-butyl peroxide. One of these photopolymerization initiators may be used alone or two or more of these photopolymerization initiators may be used in combination.

Tetramethyl ethylenediamine is used as an initiator for a polymerization/gelation reaction that transforms acrylamide into polyacrylamide gel.

The method for producing an ultrasonic propagation member of the present disclosure is roughly classified into two kinds, including a method of producing an ultrasonic propagation member using a die and a method of directly producing an ultrasonic propagation member using a three-dimensional printer.

<Producing Method Using Die>

The method of producing an ultrasonic propagation member using a the is a method of pouring the liquid material for producing an ultrasonic propagation member containing the water, the mineral, and the polymerizable monomer into a die and curing the liquid material.

In the present disclosure, the surface of the ultrasonic propagation member contacting a human body, which is the test target, has a shape conforming to the surface of the human body, which is the test target. Therefore, it is effective to produce the ultrasonic propagation member by curing the liquid material for producing an ultrasonic propagation member poured into a die, which is produced using a three-dimensional printer based on shape data of a skin surface of an examinee.

Here, having a shape conforming to the surface of the human body means having a certain shape that is convex or concave with respect to a concave portion or a convex portion of the body of an individual examinee, the concave portion or the convex portion being included in a body surface to be ultrasonographically diagnosed. This makes it possible to produce an ultrasonic propagation member that snugly fits the skin of the examinee.

The type of the three-dimensional printer is not particularly limited. However, it is preferable to produce the die using a material or a type that would not allow leakage of the liquid material for producing an ultrasonic propagation member, because the liquid material for forming an ultrasonic propagation member is injected into the die for curing. For example, an inkjet (material jet) type, a stereolithography type, and a laser sintering type can be effectively used.

In the case of using a thermal polymerization initiator for curing, the reaction temperature is controlled depending on the kind of the initiator. The liquid material for producing an ultrasonic propagation member is injected, sealed for air (oxygen) shutoff, and then heated to room temperature or a predetermined temperature to be allowed to undergo a polymerization reaction. After polymerization is completed, the resultant is taken out from the die, to obtain an ultrasonic propagation member.

In the case of using a photopolymerization initiator for curing, there is a need for irradiating the liquid material for producing an ultrasonic propagation member with an energy ray such as an ultraviolet ray, as a curing method. Therefore, the die to be used is formed of a material transparent to the energy ray. The liquid material is injected into such a die, sealed for air (oxygen) shutoff, and then irradiated with an energy ray from outside the die. After polymerization is completed in this way, the resultant is taken out from the die, to obtain an ultrasonic propagation member.

Figure 5:
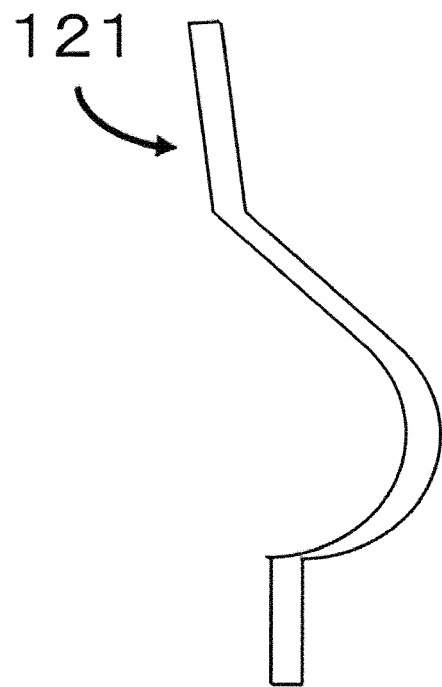
FIG. 5 is a schematic view of a male die for an ultrasonic propagation member for a breast produced with a three-dimensional printer.
Figure 6:
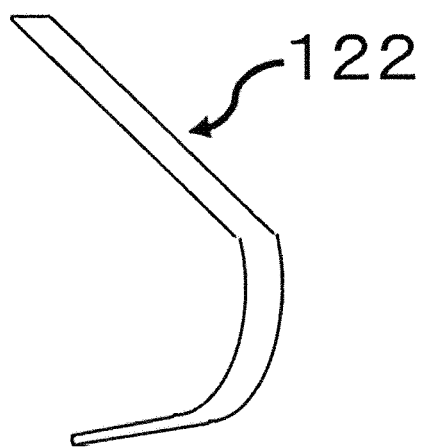
FIG. 6 is a schematic view of a female die for an ultrasonic propagation member for a breast produced with a three-dimensional printer.
Figure 7:
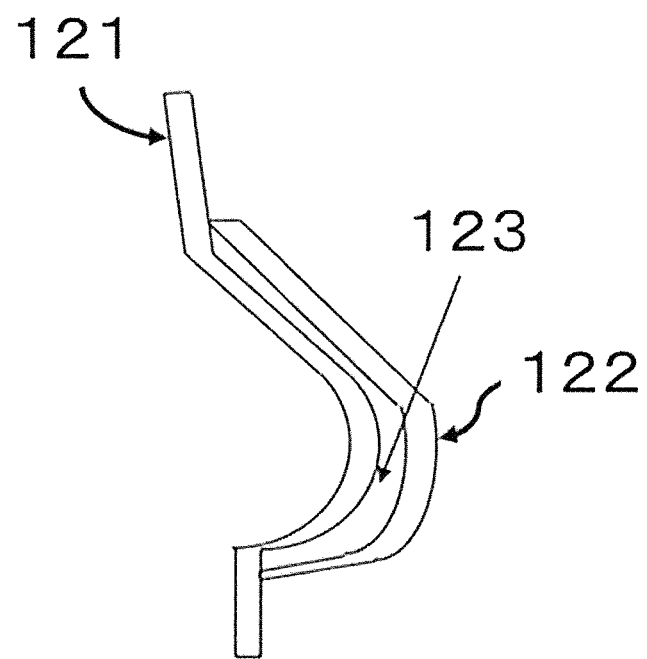
FIG. 7 is a schematic view of combined male and female dies for an ultrasonic propagation member for a breast produced with a three-dimensional printer.
Figure 8:
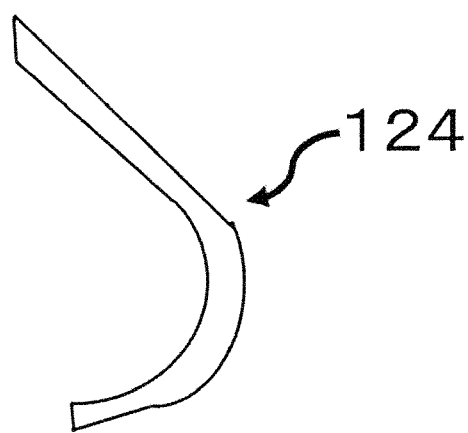
FIG. 8 is a schematic view of an ultrasonic propagation member for a breast taken out from dies.

For example, in the case of producing a die conforming to a breast shape, CT data of a breast of an examinee is acquired and converted into three-dimensional (3D) data in order that male and female dies can be produced based on the data. Based on the three-dimensional data, a male die 121 for producing a three-dimensional ultrasonic propagation member for the breast of the examinee illustrated in FIG. 5 is produced using a three-dimensional printer. Based on the examinee's personal data, a female die 122 for producing a three-dimensional ultrasonic propagation member for the breast illustrated in FIG. 6 is produced using a three-dimensional printer. When the produced male die 121 and female die 122 are combined with each other as illustrated in FIG. 7, a gap 123 is formed between both of the dies. By injecting the liquid material for producing an ultrasonic propagation member into this gap 123 and curing the liquid material, it is possible to produce a three-dimensional ultrasonic propagation member 124 for a breast illustrated in FIG. 8.

<Direct Producing Method Using Three-Dimensional Printer>

Object production using the three-dimensional printer is intended for directly producing an object using a three-dimensional printer and the liquid material for producing an ultrasonic propagation member.

It is preferable that the three-dimensional printer be a three-dimensional printer of an inkjet type or a three-dimensional printer of a stereolithography type. Use of these types enables a composition distribution or shape control that is suited to the condition of a body part to be diagnosed, of an examinee.

It is possible to impart a shape conforming to a body surface to be ultrasonographically diagnosed, using the personal data of an examinee. Also in this case, production is based on personal data of the examinee.

For example, in the case of producing a die suited to a breast shape, CT data of a breast is acquired and converted into three-dimensional (3D) data in order that male and female dies can be produced based on the data. Based on the 3D data, an ultrasonic propagation member is produced using a three-dimensional printer.

It is preferable that the three-dimensional printer be of a type that can print the liquid material for producing an ultrasonic propagation member. It is effective to use a system that is configured to discharge an ink by an inkjet (material jet) method or a dispenser method and cure the ink with UV light.

Figure 9:
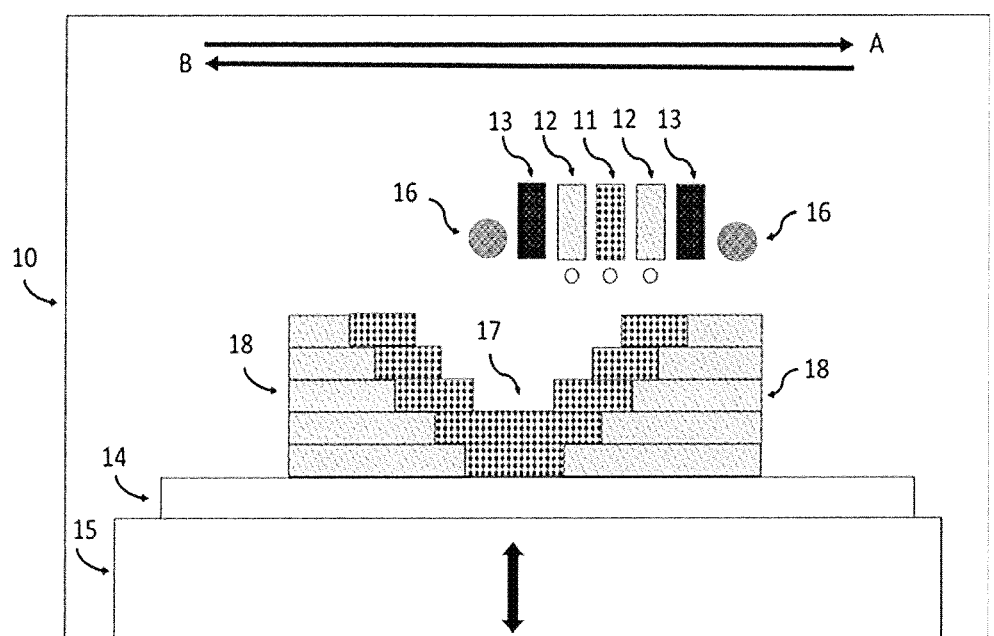
FIG. 9 is a schematic view of a three-dimensional printer configured to produce an ultrasonic propagation member.

For example, a three-dimensional printer 10 of an inkjet (IJ) type as illustrated in FIG. 9 is configured to use a head unit in which inkjet heads are arranged, and laminate layers by discharging the liquid material for producing an ultrasonic propagation member from a discharging head unit 11 for the liquid material for producing an ultrasonic propagation member, discharging a liquid material for producing a support from discharging head units 12 and 12 for the liquid material for producing a support, and curing the liquid material for producing an ultrasonic propagation member and the liquid material for producing a support with adjoining ultraviolet ray irradiators 13 and 13.

In order to maintain the discharging head unit 11 for a liquid material for producing an ultrasonic propagation member, the discharging head units 12 for the liquid material for producing a support, and the ultraviolet ray irradiators 13 at a constant gap from the ultrasonic propagation member 17 and a support 18, layer lamination is performed while a stage 15 is lifted down in accordance with the number of times of layer lamination.

In the three-dimensional printer 10, the ultraviolet ray irradiators 13 and 13 are used in moving in the directions of both of the arrows A and B. The surface of a laminated layer of the liquid material for producing a support is smoothed by the heat generated along with the ultraviolet ray irradiation. As a result, the dimensional stability of the ultrasonic propagation member can be improved.

Figure 10:
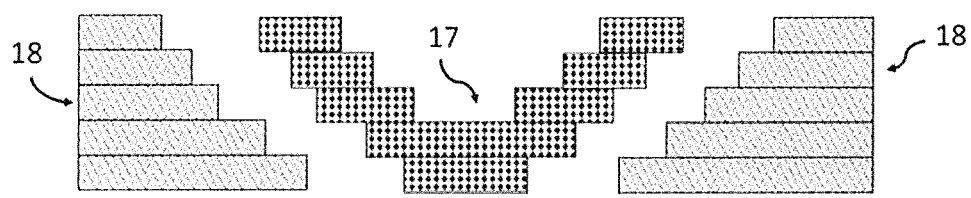
FIG. 10 is a schematic view of an ultrasonic propagation member produced with a three-dimensional printer being detached from a support.

After object production is completed, the ultrasonic propagation member 17 and the support 18 are pulled in the horizontal direction and detached from each other as illustrated in FIG. 10. As a result, the support 18 is detached as an integral body, and the ultrasonic propagation member 17 can be easily taken out.

Figure 11:
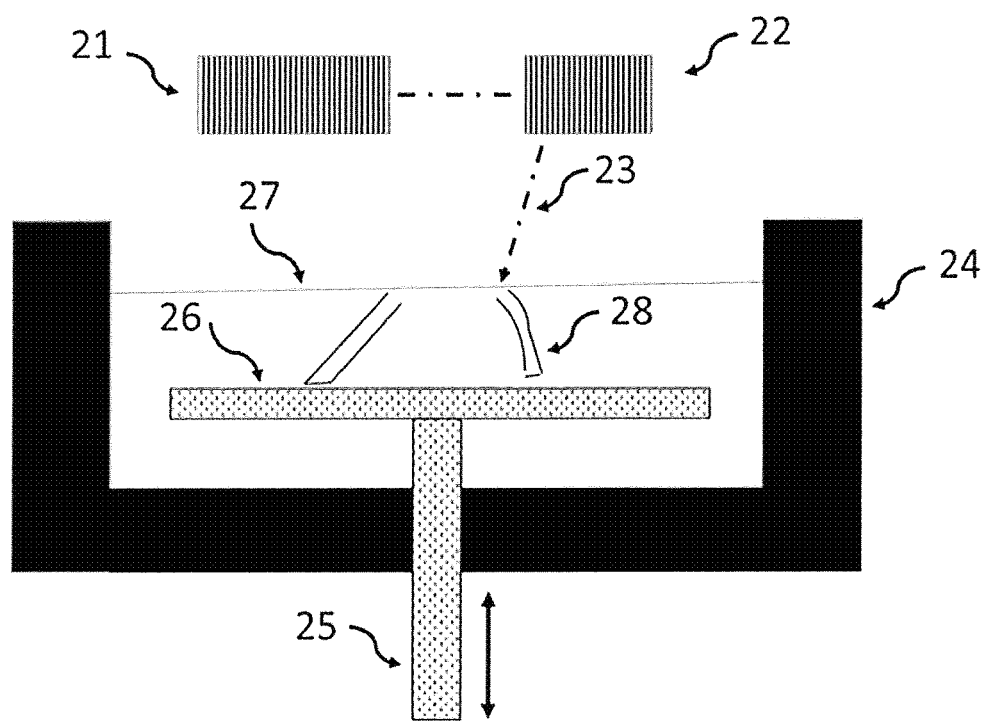
FIG. 11 is a schematic view of a three-dimensional printer having a different configuration for producing an ultrasonic propagation member.

Further, as illustrated in FIG. 11, a three-dimensional printer of a stereolithography type is configured to store the liquid material for producing an ultrasonic propagation member in a liquid tank 24, irradiate a surface 27 of the liquid tank with ultraviolet laser light emitted from a laser light source 21 through a laser scanner 22, and produce a cured product on an object production stage 26. The object production stage 26 is lifted down by means of a piston 25. Through repetition of this sequence, an ultrasonic propagation member is obtained.

<Applications of Ultrasonic Propagation Member>

The ultrasonic propagation member of the present disclosure is suitable for applications in which the ultrasonic propagation member is brought into close adhesion with a test target to test the test target in a non-destructive, non-invasive manner, because the surface of the ultrasonic propagation member contacting the test target has a shape conforming to the surface of the test target. For example, the ultrasonic propagation member can be brought into close adhesion with a skin surface, which is the test target, of the examinee without a gap and can save the examinee from a feeling of discomfort that may be felt during an ultrasonographic diagnosis and make post handling after the diagnosis unnecessary or simple. Therefore, the ultrasonic propagation member can be suitably used in an ultrasonographic diagnosis such as abdominal ultrasound scan conducted in, for example, a thorough medical checkup.

Further, the ultrasonic propagation member is useful in a method employing such a kind of probe in which an ultrasonic oscillator and an ultrasonic receiver are integrated with each other as in a typical ultrasonographic instrument.

Moreover, the ultrasonic propagation member may be used in a mode in which an ultrasonic oscillator and an ultrasonic receiver are separate devices, or may be used in combination with a device configured to input some kind of energy in order to cause a human body to emit ultrasonic waves.

Second Embodiment (Ultrasonic Propagation Member)

An ultrasonic propagation member of the present disclosure is an ultrasonic propagation member having at least two surfaces, and hardness of one surface and hardness of another surface are different.

The present disclosure has an object to provide an ultrasonic propagation member that can be brought into close adhesion with the surface of a test target without gaps and can make post handling after testing unnecessary or simple.

The present disclosure can provide an ultrasonic propagation member that can be brought into close adhesion with the surface of a test target without gaps and can make post handling after testing unnecessary or simple.

Figure 12:
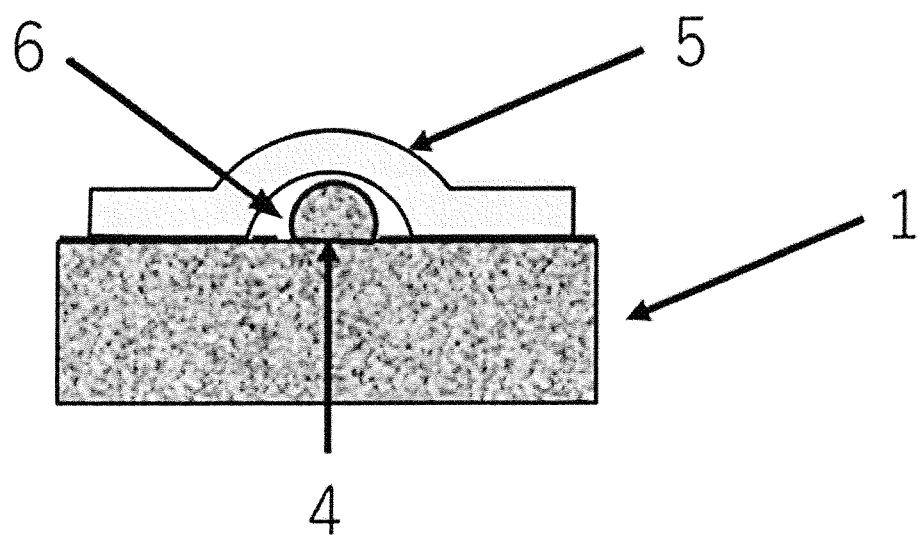
FIG. 12 is a schematic view of a case where a gel sheet having a planar structure is brought into contact with the surface of a human body.

Further, according to existing techniques, in addition to the first embodiment, a modified embodiment of the fluidic gel 2 illustrated in FIG. 1, i.e., a gel sheet 5 illustrated in FIG. 12 is known. In this case, the diagnosis is performed by placing the gel sheet 5 on the surface of the skin 1 of the examinee and pressing the gel sheet 5 by an ultrasonic receiver to make the gel sheet 5 closely adhere to the surface of the skin.

Because the gel sheet 5 has a flat plate shape produced using a die, it is difficult to bring the gel sheet 5 into complete close adhesion with the surface of the skin 1 of the examinee without a gap. Therefore, there is a drawback that a gap 6 tends to occur and bubbles tend to mix when there is a convex portion 4 over the surface of the skin as illustrated in FIG. 12. In order to make it harder for bubbles to mix, there is a need for strongly pressing the ultrasonic receiver on the human body. This may give a pain to the examinee depending on the body part.

The ultrasonic propagation member of the present disclosure has been made in view of the findings described above, and is an ultrasonic propagation member having at least two surfaces, wherein hardness of one surface and hardness of another surface are different. This saves the examinee, who is the test target, from a feeling of discomfort, and makes post handling after testing unnecessary. Further, in terms of operability, the ultrasonic propagation member has an excellent close adhesiveness and makes ultrasonographic diagnoses smooth.

The test target is not particularly limited and may be appropriately selected depending on the intended purpose. Examples of the test target include an examinee of an ultrasonographic diagnosis.

The ultrasonic propagation member of the present disclosure is an ultrasonic propagation member having at least two surfaces, wherein hardness of one surface and hardness of another surface are different. It is preferable that the another surface be a surface opposite to the one surface. It is preferable that the one surface be a surface contacting an ultrasonic receiver, and that the another surface be a surface contacting a test target. It is preferable that the hardness of the surface contacting the ultrasonic receiver be higher than the hardness of the surface contacting the test target.

Figure 13:
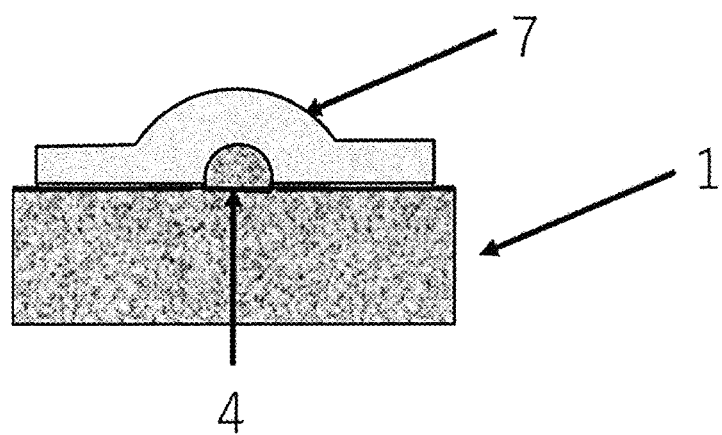
FIG. 13 is a concept view of a case where an ultrasonic propagation member of the present disclosure is bought into contact with a convex portion of the surface of a human body.

In the case of bringing the ultrasonic propagation member into contact with the surface of the human body of an examinee, who is the test target, the lower the hardness of the ultrasonic propagation member 5, the easier it is for the ultrasonic propagation member 5 to deform and closely adhere to the surface of the skin even when there is a convex portion 4 over the surface of the skin as illustrated in FIG. 13. However, if the entire body of the ultrasonic propagation member is set to that hardness, the ultrasonic propagation member is so flexible that not only is it difficult to handle the ultrasonic propagation member but also movement of the ultrasonic receiver (when slid over the surface) is hindered. Therefore, the ultrasonic receiver needs to have a certain level of hardness.

In order to build such a structure, there are two methods. One is to laminate a plurality of layers 51 and 52 different in hardness to form the ultrasonic propagation member as a laminate structure (see FIG. 14). The other is to form an ultrasonic propagation member 53 having a gradient structure with a gradually varying hardness from one surface to the opposite surface (see FIG. 15).

The ultrasonic propagation member of the present disclosure needs to have an appropriate hardness in terms of handleability and close adhesiveness with a human body. It is difficult to quantify the hardness of such a material (member) as having considerable flexibility and fracture toughness like the ultrasonic propagation member of the present disclosure. However, the hardness of such a material can be defined by Young's modulus.

A Young's modulus can be measured by, for example, mechanical testing methods, resonance methods, and ultrasonic pulse methods. Mechanical testing methods that can measure a measurand in simple manners are effective for a considerably flexible material as in the present disclosure.

The ultrasonic propagation member of the present disclosure is an ultrasonic propagation member having at least two surfaces, wherein hardness of one surface and hardness of another surface are different. It is preferable that the one surface be a surface contacting an ultrasonic receiver and that the another surface be a surface contacting a test target.

The following can be said about the surface contacting a test target. When the Young's modulus is extremely low, the ultrasonic propagation member cannot retain shape due to the deadweight and serve the function as an ultrasonic propagation member. Conversely, when the Young's modulus is extremely high, the ultrasonic propagation member may have a poor close adhesiveness with a human body, which is the test target. Therefore, the hardness of the surface contacting the test target expressed by Young's modulus is preferably 0.5 kPa or greater but 30 kPa or less and more preferably 1 kPa or greater but 20 kPa or less.

On the other hand, as for the surface contacting an ultrasonic receiver, when the Young's modulus is extremely low, the ultrasonic receiver cannot be moved over the surface of the ultrasonic propagation member smoothly, to give influence to the diagnosis. Conversely, when the surface is extremely hard, the ultrasonic propagation member has a poor close adhesiveness with the ultrasonic receiver, and cannot serve the function as an ultrasonic propagation member. Therefore, hardness of the surface contacting the ultrasonic receiver expressed by Young's modulus is preferably 10 kPa or greater but 200 kPa or less and more preferably 20 kPa or greater but 100 kPa or less.

It is preferable that the surface of the ultrasonic propagation member of the present disclosure contacting a test target have a shape conforming to the surface of the test target. As a result, the ultrasonic propagation member can fit the skin of an examinee, who is a test target, without gaps.

When it is said that the surface of the ultrasonic propagation member contacting the test target has a shape conforming to the surface of the test target, it is meant that the surface of the ultrasonic propagation member has a certain shape that is convex or concave with respect to a concave portion or a convex portion present over the surface of the test target, and there is no need for bringing the ultrasonic propagation member into close adhesion with the concave portion of the convex portion (or deforming the ultrasonic propagation member to conform to the concave portion or the convex portion) of the test target by strongly pressing the ultrasonic propagation member against the concave portion or the convex portion of the test target. For example, for the ultrasonography purpose, an ultrasonic propagation member originally having a shape matching a concave portion or a convex portion of the part, to be tested, of the human body of the examinee needs only to be positioned in alignment with the part to be tested, and can follow slight fluctuations during the diagnosis. Therefore, such an ultrasonic propagation member can contribute to an accurate, quick ultrasonographic diagnosis.

The ultrasonic propagation member of the present disclosure contains water, a polymer, and a mineral, preferably contains an organic solvent, and further contains other components as needed.

It is preferable that the ultrasonic propagation member be formed of a hydrogel that is formed by an organic solvent being contained in a three-dimensional network structure formed by the mineral, which is dispersed in the solvent, being cross-linked and combined with the polymer, which is produced from polymerization of the polymerizable monomer. The water, the polymer, the mineral, the organic solvent, and the other components of the present disclosure are the same as in the first embodiment. Therefore, description about these components will be skipped.

<Coating Film>

For example, the material, film thickness, forming method, water vapor permeability, oxygen permeability, antiseptic, hardness (Young's modulus), transmittance, and ultrasonic propagation velocity of the coating film of the present disclosure are the same as in the first embodiment. Therefore, description about these matters will be skipped.

(Method for Producing Ultrasonic Propagation Member)

A method for producing an ultrasonic propagation member of the present disclosure is a method for producing an ultrasonic propagation member using a liquid material for producing an ultrasonic propagation member containing water, a mineral, and a polymerizable monomer.

<Liquid Material for Producing Ultrasonic Propagation Member>

The liquid material for producing an ultrasonic propagation member contains water, a mineral, and a polymerizable monomer, preferably contains an organic solvent, and further contains other components as needed.

As the water, the mineral, the organic solvent, and the other components, the same materials as in the ultrasonic propagation member can be used. The polymerizable monomer of the present disclosure is the same as in the first embodiment. Therefore, description about the polymerizable monomer will be skipped.

It is preferable to cure the liquid material for producing an ultrasonic propagation member using a polymerization initiator. The polymerization initiator is added in the liquid material for producing an ultrasonic propagation member when used. The polymerization initiator of the present disclosure is the same as in the first embodiment. Therefore, description about the polymerization initiator will be skipped.

<Producing Method Using Die>

The method of producing an ultrasonic propagation member using a the is a method of pouring the liquid material for producing an ultrasonic propagation member containing the water, the mineral, and the polymerizable monomer into a die and curing the liquid material.

The feature of the ultrasonic propagation member of the present disclosure is that the ultrasonic propagation member has at least two surfaces, wherein hardness of one surface and hardness of another surface are different. It is preferable to produce an ultrasonic propagation member having a laminate structure, which is a structure including at least two layers, using a die having a desired shape.

Therefore, the ultrasonic propagation member is produced by preparing two or more kinds of liquid materials for producing an ultrasonic propagation member capable of producing hydrogels different in hardness, and performing a plurality of times a step of pouring the liquid materials into a die and curing the liquid materials sequentially.

Figure 16:
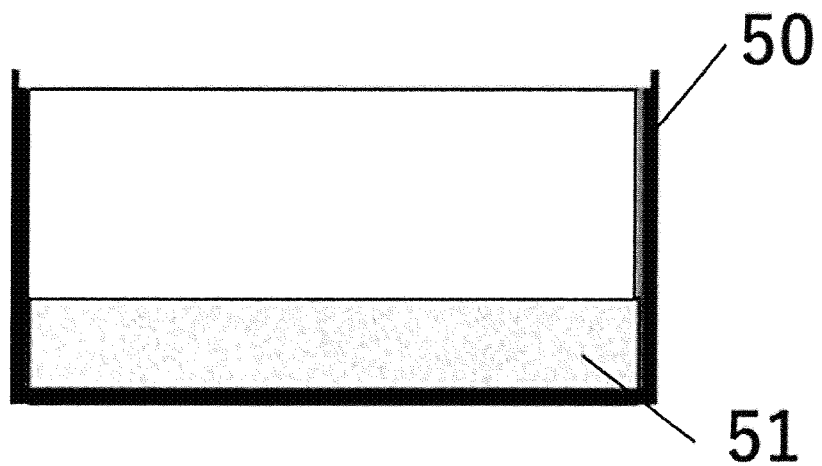
FIG. 16 is a view illustrating an example of a method for producing an ultrasonic propagation member of the present disclosure having a laminate structure.
Figure 17:
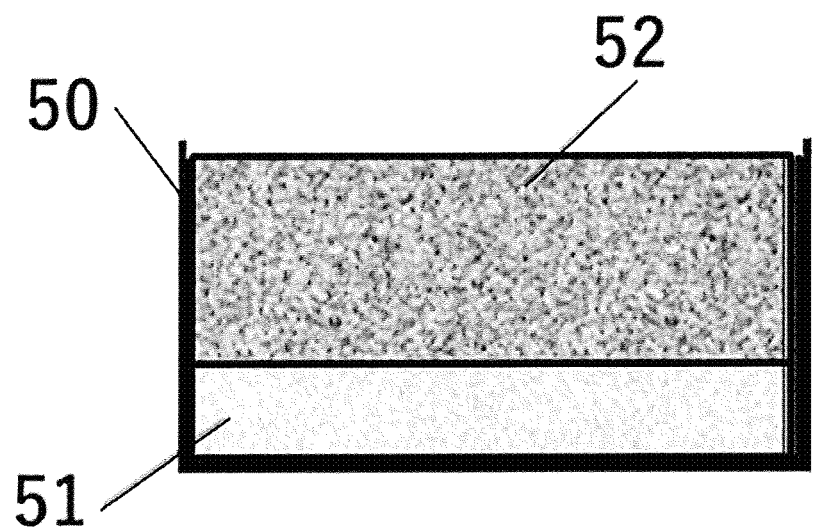
FIG. 17 is a view illustrating a method for producing an ultrasonic propagation member of the present disclosure having a laminate structure.

For example, as illustrated in FIG. 16, a desired die 50 is prepared, and a liquid material 51 for producing an ultrasonic propagation member having a high hardness when cured (for producing a surface contacting an ultrasonic receiver) is poured into the die and cured. Next, as illustrated in FIG. 17, a liquid material 52 for producing an ultrasonic propagation member having a low hardness (for producing a surface contacting a human body) is poured onto the resultant and cured. The resultant is taken out from the die, to obtain the ultrasonic propagation member of the present disclosure.

In the present disclosure, it is further effective to produce the ultrasonic propagation member by curing the liquid material for producing an ultrasonic propagation member poured into a die, which is produced using a three-dimensional printer based on shape data of a skin surface of an examinee.

Here, having a shape conforming to the body surface means having a certain shape that is convex or concave with respect to a concave portion or a convex portion of the body of an individual examinee, the concave portion or the convex portion being included in a body surface to be ultrasonographically diagnosed. This makes it possible to produce an ultrasonic propagation member that snugly fits the skin of the examinee.

The type of the three-dimensional printer is not particularly limited, as in the first embodiment. For example, a case of using a thermal polymerization initiator for curing, a case of using a photopolymerization initiator for curing, and a case of producing a die matching a breast shape according to the present disclosure are the same as in the first embodiment. Therefore, description about these cases will be skipped.

<Direct Producing Method Using Three-Dimensional Printer>

Object production using the three-dimensional printer is intended for directly producing an object using a three-dimensional printer and the liquid material for producing an ultrasonic propagation member.

It is preferable that the three-dimensional printer be a three-dimensional printer of an inkjet type or a three-dimensional printer of a stereolithography type. Use of these types enables a composition distribution or shape control that is suited to the condition of a body part to be diagnosed, of an examinee.

Figure 14:
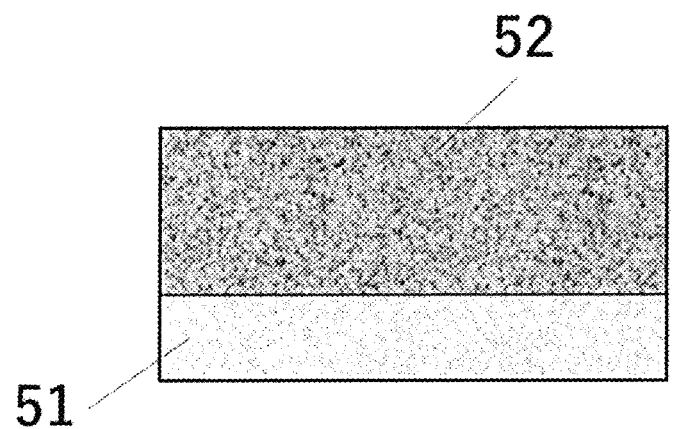
FIG. 14 is a cross-sectional view of an ultrasonic propagation member of the present disclosure.
Figure 15:
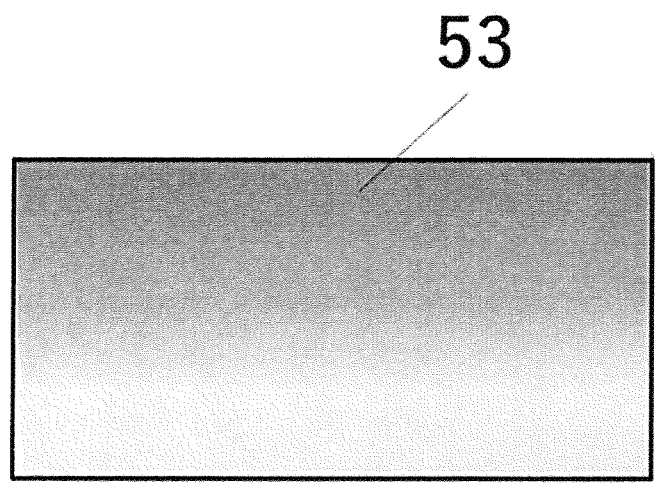
FIG. 15 is a cross-sectional view of an ultrasonic propagation member of the present disclosure having a different configuration.

For this reason, it is possible to produce an ultrasonic propagation member as illustrated in FIG. 14 and including a plurality of laminated layers different in hardness or an ultrasonic propagation member as illustrated in FIG. 15 and having a hardness gradient.

Further, it is possible to produce an ultrasonic propagation member having a shape conforming to a body surface to be ultrasonically diagnosed, using personal data of an examinee. Also in this case, the production is based on the data of an individual examinee.

For example, in the case of producing a die conforming to a breast shape, CT data of a breast is acquired and converted into three-dimensional (3D) data in order that male and female dies can be produced based on the data. Based on this 3D data, an ultrasonic propagation member is directly produced using a three-dimensional printer.

It is preferable that the three-dimensional printer be of a type that can print the material of an ultrasonic propagation member. It is effective to use a system that is configured to discharge an ink by an inkjet (material jet) method or a dispenser method and cure the ink with UV light.

Here, an inkjet (Id) three-dimensional printer 10 as illustrated in FIG. 9 can be used as in the first embodiment.

<Applications of Ultrasonic Propagation Member>

The ultrasonic propagation member of the present disclosure is suitable for applications in which the ultrasonic propagation member is brought into close adhesion with a test target to test the test target in a non-destructive, non-invasive manner, because the ultrasonic propagation member has at least two surfaces and hardness of one surface and hardness of another surface are different. For example, the ultrasonic propagation member can be brought into close adhesion with a skin surface, which is the test target, of the examinee without a gap and can save the examinee from a feeling of discomfort that may be felt during an ultrasonographic diagnosis and make post handling after the diagnosis unnecessary or simple. Therefore, the ultrasonic propagation member can be suitably used in an ultrasonographic diagnosis such as abdominal ultrasound scan conducted in, for example, a thorough medical checkup.

Further, the ultrasonic propagation member is useful in a method employing such a kind of probe in which an ultrasonic oscillator and an ultrasonic receiver are integrated with each other as in a typical ultrasonographic instrument.

Moreover, the ultrasonic propagation member may be used in a mode in which an ultrasonic oscillator and an ultrasonic receiver are separate devices, or may be used in combination with a device configured to input some kind of energy in order to cause a human body to emit ultrasonic waves.

EXAMPLES

The present disclosure will be described below by way of Examples. The present disclosure should not be construed as being limited to these Examples.

Example 1

—Production of Die—

CT data of the surface of a breast of a patient (treatment recipient) was converted into data for three-dimensional (3D) printing. Based on this data, a male the 121 and a female die 122 for a three-dimensional ultrasonic propagation member for the breast as illustrated in FIG. 5 and FIG. 6 were produced using AGILISTA available from Keyence Corporation as an inkjet stereolithography apparatus.

—Preparation of Liquid Material for Producing Ultrasonic Propagation Member—

First, to pure water (200 parts by mass) under stirring, synthetic hectorite (LAPONITE XLG, available from Rock Wood) having a composition $[Mg_{5.34}Li_{0.66}Si_8O_{20}(OH)_4]$ $Na^-_{0.66}$ (15 parts by mass) was added little by little as a water-swellable layered clay mineral, and then 1-hydroxyethane-1,1-diphosphonic acid (0.8 parts by mass) was further added, followed by stirring, to prepare a dispersion liquid.

Next, to the obtained dispersion liquid, acryloylmorpholine (available from KJ Chemicals Corporation) (20 parts by mass) having been passed through an activated alumina column for removal of a polymerization inhibitor and LIGHT ACRYLATE 9EG-A (available from Kyoeisha Chemical Co., Ltd.) (1 part by mass) were added as polymerizable monomers.

Next, to the resultant under cooling in an ice bath, a 2% by mass aqueous solution (15 parts by mass) of sodium peroxodisulfate (available from Wako Pure Chemical Industries, Ltd.) in pure water was added, and tetramethyl ethylenediamine (available from Wako Pure Chemical Industries, Ltd.) (1 part by mass) was further added, followed by stirring and mixing, and then vacuum degassing for 10 minutes. Subsequently, the resultant was subjected to filtration to remove, for example, impurities, to obtain a homogeneous liquid material for producing an ultrasonic propagation member.

—Production of Three-Dimensional Ultrasonic Propagation Member for Breast—

The male die 121 and the female die 122 produced before were combined with each other as illustrated in FIG. 7, the liquid material for producing an ultrasonic propagation member was poured into the die, capped for sealing, and subjected to curing reaction at room temperature for 6 hours. After curing, the resultant was taken out from the die and washed with water, to obtain a three-dimensional ultrasonic propagation member for the breast. The thickness was roughly 1 cm.

Example 2

A three-dimensional ultrasonic propagation member for a breast was produced in the same manner as in Example 1, except that the amount of pure water was changed from 200 parts by mass to 400 parts by mass, unlike in Example 1.

Example 3

A three-dimensional ultrasonic propagation member for a breast was produced in the same manner as in Example 1, except that the amount of pure water was changed from 200 parts by mass to 660 parts by mass, unlike in Example 1.

Example 4

A three-dimensional ultrasonic propagation member for a breast was produced in the same manner as in Example 1, except that the amount of pure water was changed from 200 parts by mass to 2,000 parts by mass, unlike in Example 1.

Example 5

A three-dimensional ultrasonic propagation member for a breast was produced in the same manner as in Example 1, except that the amount of pure water was changed from 200 parts by mass to 170 parts by mass, unlike in Example 1.

Example 6

A three-dimensional ultrasonic propagation member for a breast was produced in the same manner as in Example 2, except that 100 parts by mass out of 400 parts by mass of pure water was changed to glycerin, unlike in Example 2.

Example 7

A three-dimensional ultrasonic propagation member for a breast was produced in the same manner as in Example 6, except that 10 parts by mass out of 20 parts by mass of acryloylmorpholine serving as a polymerizable monomer was changed to N,N-dimethyl acrylamide (available from Wako Pure Chemical Industries, Ltd.), unlike in Example 6.

Example 8

An ultrasonic propagation member was produced in the same manner as in Example 2, except that PLASTICOAT #100 (available from Daikyo Chemical Co., Ltd.) was coated over the surface of the ultrasonic propagation member produced in Example 2 by a dip coating method, to form a coating film having a thickness of 30 micrometers.

Comparative Example 1

An ultrasonic propagation member was produced according to the description in Examples of Japanese Unexamined Patent Application Publication No. 03-272750. That is, polyvinyl alcohol (PVA) powder (with a degree of polymerization of 1,700 and a degree of saponification of 99.5%) was added to ion-exchanged water and heated to 60 degrees C., to produce a PVA aqueous solution having a PVA concentration of 10% by mass. This aqueous solution was injected into a die having a length of 6 cm on each side and a thickness of 4 mm, freezed at −20 degrees C., and subsequently thawed at room temperature, to produce a flexible gel sheet having a water content of 90%.

Comparative Example 2

As Comparative Example 2, gel for ultrasonography commonly used (available from Jex Inc., PROJELLY) was evaluated in terms of only the items (6) and (7) described below.

Next, hardness (Young's modulus), transmittance, and ultrasonic propagation velocity of the ultrasonic propagation members produced in Example 1 to 8 and Comparative Example 1 were measured in the manners described below. The results are presented in Table 1.

<Hardness (Young's Modulus)>

Hardness (Young's modulus) was measured three times using a flexibility measuring system (available from Horiuchi Electronics Co., Ltd., SOFTMEASURE HANDY TYPE HG1003) at 25 degrees C. at 50% RH, and an average value was obtained.

<Transmittance>

Transmittance was measured using a spectrophotometer (available from Hitachi, Ltd., UV-3100) at 25 degrees C. at 50% RH. An average transmittance in the wavelength range of 400 nm or longer but 700 nm or shorter was obtained as transmittance of each ultrasonic propagation member.

<Ultrasonic Propagation Velocity>

Ultrasonic propagation velocity was measured according to the method described in JIS Z 2353. The measuring temperature was fixed at 22 degrees C.

<Evaluation of Other Various Properties>

The three-dimensional ultrasonic propagation members for a breast produced in Examples 1 to 8 and Comparative Example 1 and the three-dimensional gel for ultrasonography for a breast of Comparative Example 2 were evaluated in terms of the following testing items. The results are presented in Table 2.

(1) Appearance

Appearance of each of the three-dimensional ultrasonic propagation member for a breast was evaluated according to the criteria described below.

[Evaluation Criteria]

B: Transparency was high, and no bubbles were mixed.
C: Transparency was slightly low.
D: Transparency was low.

(2) Dimensions

Dimensions of each of the three-dimensional ultrasonic propagation members for a breast were evaluated according to the criteria described below.

[Evaluation Criteria]

B: The thickness and the length were uniform.
D: The thickness and the length were nonuniform.

(3) Elasticity

Elasticity of each of the three-dimensional ultrasonic propagation members for a breast was evaluated according to the criteria described below.

[Evaluation Criteria]

A: The three-dimensional ultrasonic propagation member had an appropriate elasticity and did not undergo changes such as tearing even when folded by 180 degrees.
B: The three-dimensional ultrasonic propagation member had an appropriate elasticity.
D: The three-dimensional ultrasonic propagation member had a low elasticity and was torn when folded by 180 degrees.

(4) Heat Resistance

After each of the three-dimensional ultrasonic propagation members for a breast was heated in hot water of 60 degrees C. for 30 minutes, the shape and physical properties were measured and evaluated according to the criteria described below.

[Evaluation Criteria]

B: The shape and physical properties did not change.
D: The shape and physical properties deteriorated.

(5) Solvent Resistance

After each of the three-dimensional ultrasonic propagation members for a breast was washed with ethanol, the shape and physical properties were measured and evaluated according to the criteria described below.

[Evaluation Criteria]

B: The shape and physical properties did not change.
C: The three-dimensional ultrasonic propagation member slightly swelled.
D: The shape and physical properties deteriorated.

(6) Close Adhesiveness with Surface of Human Body

Each of the three-dimensional ultrasonic propagation members for a breast was brought into contact with a skin surface of an examinee, to evaluate the degree of close adhesiveness according to the criteria described below.

[Evaluation Criteria]

B: The three-dimensional ultrasonic propagation member closely adhered to skin of a human body having convexes and concaves without bubbles.
D: The three-dimensional ultrasonic propagation member did not completely closely adhere to skin of a human body having convexes and concaves, and there were gaps.

(7) State During Close Adhesion and Post Handling After Evaluation

The state during close adhesion of each of the three-dimensional ultrasonic propagation members for a breast and post handling after evaluation were evaluated according to the criteria described below.

[Evaluation Criteria]

B: Because the three-dimensional ultrasonic propagation member snugly fitted, there was no need for pressing and the examinee did not feel a pain. Because there was no residue, there was no need for wiping off.
C: Because the three-dimensional ultrasonic propagation member poorly fitted at convexes and concaves, there was a need for strongly pressing the ultrasonic detector and the examinee felt a feeling of wrongness. Because there was no residue, there was no need for wiping off.
D: After evaluation, there was a residue on the skin and there was a need for wiping off. The examinee felt a feeling of wrongness.

(8) Storage Stability

After each of the three-dimensional ultrasonic propagation members for a breast was stored for 7 days in a sealed state (at 25 degrees C. and 50% RH), the shape and physical properties were measured, to evaluate storage stability according to the criteria described below.

[Evaluation Criteria]

A: The shape and physical properties did not change.
B: The three-dimensional ultrasonic propagation member did not undergo a shape change, and slightly dried (with a weight change rate of within 3%.
D: The shape and physical properties deteriorated.

TABLE 1

| | Coating film | Hardness (Young's modulus) (kPa) | Transmittance (%) | Ultrasonic propagation velocity (m/s) |
|---|---|---|---|---|
| Ex. 1 | Absent | 75 | 95 | 1,575 |
| Ex. 2 | Absent | 17 | 90 | 1,530 |
| Ex. 3 | Absent | 3 | 70 | 1,510 |
| Ex. 4 | Absent | 0.8 | 40 | 1,500 |
| Ex. 5 | Absent | 105 | 95 | 1,585 |
| Ex. 6 | Absent | 16 | 90 | 1,530 |
| Ex. 7 | Absent | 15 | 90 | 1,530 |
| Ex. 8 | Present | 18 | 90 | 1,530 |
| Comp. Ex. 1 | Absent | 50 | 65 | 1,505 |

TABLE 2

| | Appearance | Dimensions | Elasticity | Heat resistance | Solvent resistance | Close adhesiveness | Post handling | Storage stability |
|---|---|---|---|---|---|---|---|---|
| Ex. 1 | B | B | B | B | B | B | B | B |
| Ex. 2 | B | B | B | B | B | B | B | B |

TABLE 2-continued

|  | Appearance | Dimensions | Elasticity | Heat resistance | Solvent resistance | Close adhesiveness | Post handling | Storage stability |
|---|---|---|---|---|---|---|---|---|
| Ex. 3 | C | B | B | B | B | A | B | B |
| Ex. 4 | C | B | B | B | B | B | C | B |
| Ex. 5 | B | B | B | B | B | C | B | B |
| Ex. 6 | B | B | B | B | B | B | B | A |
| Ex. 7 | B | B | A | B | B | A | B | B |
| Ex. 8 | B | B | B | B | B | B | B | A |
| Comp. Ex. 1 | D | B | B | B | B | D | C | B |
| Comp. Ex. 2 | — | — | — | — | — | D | D | — |

(9) Evaluation of Image

Using the ultrasonic propagation members produced in Examples 1 to 8, image diagnoses were performed using an ultrasonographic instrument. With any of the ultrasonic propagation members, a clear image was obtained.

However, in the case of Example 4, there was a slight residue and wiping off was needed.

In the case of Example 5, there was a part, of which image was hard to capture unless the ultrasonic detector was pressed strongly.

Moreover, when minute portions in the image were compared, it was revealed that there was a part with a very slightly poor resolution.

Example 9

—Preparation of Liquid Material for Producing Ultrasonic Propagation Member—

First, to pure water (330 parts by mass) under stirring, synthetic hectorite (LAPONITE XLG, available from Rock Wood) having a composition [$Mg_{5.34}Li_{0.66}Si_8O_{20}(OH)_4$] $Na^-_{0.66}$ (16 parts by mass) was added little by little as a water-swellable layered clay mineral, followed by stirring for 3 hours, to produce a dispersion liquid. Subsequently, to the resultant, 1-hydroxyethane-1,1-diphosphonic acid (available from Tokyo Kasei Corporation) (0.6 parts by mass) was added, followed by stirring for 1 hour. Subsequently, to the resultant, glycerin (available from Sakamoto Yakuhin Kogyo Co., Ltd.) (60 parts by mass) was added, followed by stirring for 10 minutes.

Next, to the obtained dispersion liquid, acryloylmorpholine (available from KJ Chemicals Corporation) (16 parts by mass) having been passed through an activated alumina column for removal of a polymerization inhibitor, N,N-dimethyl acrylamide (available from Wako Pure Chemical Industries, Ltd.) (4 parts by mass), and LIGHT ACRYLATE 9EG-A (available from Kyoeisha Chemical Co., Ltd.) (1 part by mass) were added as polymerizable monomers. To the resultant, EMULGEN SLS-106 (available from Kao Corporation) (1 part by mass) was further added as a surfactant and mixed.

Next, to the resultant under cooling in an ice bath, a 4% by mass methanol solution (2.2 parts by mass) of a photopolymerization initiator (IRGACURE 184, available from BASF GmbH) was added, followed by stirring and mixing, and then vacuum degassing for 20 minutes. Subsequently, the resultant was subjected to filtration to remove, for example, impurities, to obtain a liquid material for producing an ultrasonic propagation member.

—Preparation of Liquid Material for Producing Support—

Urethane acrylate (available from Mitsubishi Rayon Co., Ltd., product name: DIABEAM UK6038) (10 parts by mass), neopentyl glycol hydroxypivalic acid ester di(meth) acrylate (available from Nippon Kayaku Co., Ltd., product name: KAYARAD MANDA) (90 parts by mass) as a polymerizable monomer, and 1-hydroxycyclohexyl phenyl ketone (available from BASF GmbH, product name: IRGACURE 184) (3 parts by mass) as a polymerization initiator were subjected to dispersion treatment using a homogenizer (available from Hitachi Koki Co., Ltd., HG30) at a number of rotations of 2,000 rpm until a homogeneous mixture was obtained. Subsequently, the mixture was subjected to filtration to remove, for example, impurities, and finally subjected to vacuum degassing for 10 minutes, to obtain a homogeneous liquid material for producing a support.

Production of 3D Ultrasonic Propagation Member—

The liquid material for producing an ultrasonic propagation member and the liquid material for producing a support were filled in two inkjet heads (available from Ricoh Industry Company, Ltd., GEN 4) of an inkjet three-dimensional printer as illustrated in FIG. 9 and discharged, to form films.

As in the case of Example 1, CT data of the surface of a breast of a patient (treatment recipient) was converted into data for 3D printing. Based on this data, an ultrasonic propagation member was produced.

Using an ultraviolet ray irradiator (available from Ushio Inc., SPOT CURE SP5-250DB), the liquid material for producing an ultrasonic propagation member and the liquid material for producing a support were irradiated and cured with a light volume of 350 mJ/$cm^2$, to produce an ultrasonic propagation member and a support.

After production, the ultrasonic propagation member 17 and the support 18 were drawn in the horizontal direction and separated from each other as illustrated in FIG. 10. As a result, the support 18 was separated as an integrated body, and the ultrasonic propagation member 17 could be easily taken out. In this way, a three-dimensional ultrasonic propagation member for a breast was produced.

Example 10

A three-dimensional ultrasonic propagation member for a breast was produced in the same manner as in Example 9, except that 0.5 parts by mass out of 1 part by mass of LIGHT ACRYLATE 9EG-A (available from Kyoeisha Chemical Co., Ltd.) in the liquid material for producing an ultrasonic propagation member of Example 9 was changed to N,N-methylene bisacrylamide (available from Wako Pure Chemical Industries, Ltd.).

Example 11

POVAL 205 (available from Kuraray Co., Ltd.) was coated over the surface of the three-dimensional ultrasonic propagation member for a breast produced in Example 9 by a clip coating method, to form a coating film having a thickness of 30 micrometers.

Example 12

Using the stereolithography three-dimensional printer illustrated in FIG. 11, the liquid material for producing an ultrasonic propagation member produced in Example 9 was irradiated and cured with a light volume of 350 mJ/cm$^2$ using a laser (available from Coherent Inc., with a wavelength of 375 nm), to produce a three-dimensional ultrasonic propagation member for a breast.

Next, hardness (Young's modulus), transmittance, ultrasonic propagation velocity, and other various properties of the three-dimensional ultrasonic propagation members for a breast produced in Example 9 to 12 were evaluated in the same manners as in Example 1. The results are presented in Tables 3 and 4.

TABLE 3

| | Coating film | Hardness (Young's modulus) (kPa) | Transmittance (%) | Ultrasonic propagation velocity (m/s) |
|---|---|---|---|---|
| Ex. 9 | Absent | 16 | 90 | 1,535 |
| Ex. 10 | Absent | 15 | 91 | 1,535 |
| Ex. 11 | Present | 17 | 89 | 1,535 |
| Ex. 12 | Absent | 17 | 90 | 1,535 |

TABLE 4

| | Appearance | Dimensions | Elasticity | Heat resistance | Solvent resistance | Close adhesiveness | Post handling | Storage stability |
|---|---|---|---|---|---|---|---|---|
| Ex. 9 | B | B | B | B | B | B | B | B |
| Ex. 10 | B | B | A | B | B | B | B | B |
| Ex. 11 | B | B | B | B | B | B | B | A |
| Ex. 12 | B | B | B | B | B | B | B | B |

(9) Evaluation of Image

Using the ultrasonic propagation members produced in Examples 9 to 12, image diagnoses were performed using an ultrasonographic instrument. With any of the ultrasonic propagation members, an image that was clear even at minute portions was obtained.

Preparation Example 1

—Preparation of Liquid Material A for Producing Ultrasonic Propagation Member—

A liquid material A for producing an ultrasonic propagation member was prepared in the same manner as in <Preparation of liquid material for producing ultrasonic propagation member> of Example 1.

Preparation Example 2

—Preparation of Liquid Material B for Producing Ultrasonic Propagation Member—

A liquid material B for producing an ultrasonic propagation member was prepared in the same manner as in Preparation example 1, except that the amount of pure water was changed from 200 parts by mass to 400 parts by mass unlike in Preparation example 1.

Preparation Example 3

—Preparation of Liquid Material C for Producing Ultrasonic Propagation Member—

A liquid material C for producing an ultrasonic propagation member was prepared in the same manner as in Preparation example 1, except that the amount of pure water was changed from 200 parts by mass to 660 parts by mass unlike in Preparation example 1.

Preparation Example 4

—Preparation of Liquid Material D for Producing Ultrasonic Propagation Member—

A liquid material D for producing an ultrasonic propagation member was prepared in the same manner as in Preparation example 1, except that the amount of pure water was changed from 200 parts by mass to 330 parts by mass unlike in Preparation example 1.

Preparation Example 5

—Preparation of Liquid Material E for Producing Ultrasonic Propagation Member—

A liquid material E for producing an ultrasonic propagation member was prepared in the same manner as in Preparation example 1, except that 50 parts by mass out of 200 parts by mass of pure water was changed to glycerin unlike in Preparation example 1.

Preparation Example 6

—Preparation of Liquid Material F for Producing Ultrasonic Propagation Member—

A liquid material F for producing an ultrasonic propagation member was prepared in the same manner as in Preparation example 1, except that 10 parts by mass out of 20 parts by mass of acryloyl morpholine as a polymerizable monomer was changed to N,N-dimethyl acrylamide (available from Wako Pure Chemical Industries, Ltd.) unlike in Preparation example 1.

Preparation Example 7

—Preparation of Liquid Material G for Producing Ultrasonic Propagation Member—

A liquid material G for producing an ultrasonic propagation member was prepared in the same manner as in Preparation example 1, except that the amount of pure water was changed from 200 parts by mass to 2,000 parts by mass unlike in Preparation example 1.

Preparation Example 8

—Preparation of Liquid Material H for Producing Ultrasonic Propagation Member—

A liquid material H for producing an ultrasonic propagation member was prepared in the same manner as in Preparation example 1, except that the amount of pure water was changed from 200 parts by mass to 170 parts by mass unlike in Preparation example 1.

Example 101

First, a container having a size of 10 cm on each side (with a depth of 3 cm) was prepared, and using this container as a die, an ultrasonic propagation member having a flat plate shape was produced in a manner that a side facing the bottom of the container (i.e., a lower side) would be the surface contacting a test target.

The liquid material C for producing an ultrasonic propagation member was poured into the container to a depth of 1 cm, and cured for 2 hours under a condition purged with nitrogen. Next, the liquid material A for producing an ultrasonic propagation member was poured to a depth of 1 cm, and cured for 2 hours under a condition purged with nitrogen likewise. The resultant was taken out from the die, to produce an ultrasonic propagation member.

Example 102

An ultrasonic propagation member was produced in the same manner as in Example 101, except that the liquid material B for producing an ultrasonic propagation member was used instead of the liquid material C for producing an ultrasonic propagation member unlike in Example 101.

Example 103

An ultrasonic propagation member was produced in the same manner as in Example 101, except that the liquid material D for producing an ultrasonic propagation member was used instead of the liquid material A for producing an ultrasonic propagation member unlike in Example 101.

Example 104

An ultrasonic propagation member was produced in the same manner as in Example 103, except that the liquid material G for producing an ultrasonic propagation member was used instead of the liquid material D for producing an ultrasonic propagation member unlike in Example 103.

Example 105

An ultrasonic propagation member was produced in the same manner as in Example 103, except that the liquid material H for producing an ultrasonic propagation member was used instead of the liquid material D for producing an ultrasonic propagation member unlike in Example 103.

Example 106

An ultrasonic propagation member was produced in the same manner as in Example 101, except that the liquid material E for producing an ultrasonic propagation member was used instead of the liquid material A for producing an ultrasonic propagation member unlike in Example 101.

Example 107

An ultrasonic propagation member was produced in the same manner as in Example 101, except that the liquid material F for producing an ultrasonic propagation member was used instead of the liquid material A for producing an ultrasonic propagation member unlike in Example 101.

Example 108

An ultrasonic propagation member was produced in the same manner as in Example 101, except that PLASTICOAT #100 (available from Daikyo Chemical Co., Ltd.) was coated over the surface of the ultrasonic propagation member produced in Example 101 by a clip coating method, to form a coating film having a thickness of 30 micrometers.

(Comparative Example 101
—Production of Gel Sheet—

An ultrasonic propagation member was produced according to the description in Examples of Japanese Unexamined Patent Application Publication No. 03-272750. That is, polyvinyl alcohol (PVA) powder (with a degree of polymerization of 1,700 and a degree of saponification of 99.5%) was added to ion-exchanged water and heated to 60 degrees C., to produce a PVA aqueous solution having a PVA concentration of 10% by mass. This aqueous solution was injected into a die having a length of 6 cm on each side and a thickness of 4 mm, freezed at −20 degrees C., and subsequently thawed at room temperature (25 degrees C.), to produce a flexible gel sheet having a water content of 90%.

Comparative Example 102

As Comparative Example 2, gel for ultrasonography commonly used (available from Jex Inc., PROJELLY) was evaluated in terms of only the items (6) and (7) described below.

Next, hardness (Young's modulus), transmittance, and ultrasonic propagation velocity of the ultrasonic propagation members produced in Example 101 to 108 and Comparative Example 101 were measured in the manners described below. The results are presented in Table 5.

<Hardness (Young's Modulus)>

Hardness (Young's modulus) was measured using a flexibility measuring system (available from Horiuchi Electronics Co., Ltd., SOFTMEASURE HANDY TYPE HG1003) at 25 degrees C. at 50% RH. The surface contacting a human body and the surface contacting an ultrasonic receiver were each measured three times, and an average value of each was obtained.

<Transmittance>

Transmittance was measured in the same manner as in Example 1.

<Ultrasonic Propagation Velocity>

Ultrasonic propagation velocity was measured according to the method described in JIS Z 2353. The measuring temperature was fixed at 22 degrees C. Ultrasonic propagation velocity was measured in the same manner as in Example 1.

<Evaluation of Other Various Properties>

The ultrasonic propagation members produced in Examples 101 to 108 and Comparative Example 101 and the gel for ultrasonography of Comparative Example 102 were evaluated in terms of the following testing items. The results are presented in Table 6.

(1) Appearance, (2) dimensions, (3) elasticity, (4) heat resistance, (5) solvent resistance, (6) close adhesiveness with surface of human body, (7) state during close adhesion and post handling after evaluation, (8) storage stability of each of the ultrasonic propagation members were evaluated according to the same criteria as in the first embodiment.

TABLE 5

| | Liquid material for producing ultrasonic propagation member | Coating film | Hardness (Young's modulus) (kPa) Surface contacting human body | Surface contacting ultrasonic receiver | Transmittance (%) | Ultrasonic propagation velocity (m/s) |
|---|---|---|---|---|---|---|
| Ex. 101 | C, A | Absent | 3 | 75 | 80 | 1,565 |
| Ex. 102 | B, A | Absent | 17 | 75 | 93 | 1,570 |
| Ex. 103 | C, D | Absent | 3 | 21 | 75 | 1,540 |
| Ex. 104 | C, G | Absent | 0.8 | 21 | 50 | 1,535 |
| Ex. 105 | C, H | Absent | 3 | 105 | 80 | 1,580 |
| Ex. 106 | C, E | Absent | 3 | 73 | 93 | 1,530 |
| Ex. 107 | C, F | Absent | 3 | 70 | 93 | 1,565 |
| Ex. 108 | C, A | Present | 3 | 75 | 80 | 1,565 |
| Comp. Ex. 101 | Japanese Unexamined Patent Application Publication No. 03-272750 | Absent | 50 | | 65 | 1,510 |

TABLE 6

| | Appearance | Dimensions | Elasticity | Heat resistance | Solvent resistance | Close adhesiveness | Post handling | Storage stability |
|---|---|---|---|---|---|---|---|---|
| Ex. 101 | B | B | B | B | B | B | B | B |
| Ex. 102 | B | B | B | B | B | B | B | B |
| Ex. 103 | B | B | B | B | B | B | B | B |
| Ex. 104 | C | B | B | B | B | A | C | B |
| Ex. 105 | B | B | B | B | B | B | C | B |
| Ex. 106 | B | B | B | B | B | B | B | A |
| Ex. 107 | B | B | A | B | B | A | C | B |
| Ex. 108 | B | B | B | B | B | B | B | A |
| Comp. Ex. 101 | D | B | B | B | B | D | C | B |
| Comp. Ex. 102 | — | — | — | — | — | D | D | — |

(9) Evaluation of Image

Using the ultrasonic propagation members produced in Examples 101 to 108, image diagnoses were performed using an ultrasonographic instrument. With any of the ultrasonic propagation members, a clear image was obtained.

In the case of Example 105, there was a part, of which image was hard to capture unless the ultrasonic detector was pressed strongly. Moreover, when minute portions in the image were compared, it was revealed that there was a part with a very slightly poor resolution.

Example 109

—Production of Die—

CT data of the surface of a breast of a patient (treatment recipient) was converted into data for three-dimensional (3D) printing. Based on this data, a male the 121 and a female die 122 for a three-dimensional ultrasonic propagation member for the breast as illustrated in FIG. 5 and FIG. 6 were produced using AGILISTA available from Keyence Corporation as an inkjet stereolithography apparatus.

—Production of Three-Dimensional Ultrasonic Propagation Member for Breast—

The liquid material A for producing an ultrasonic propagation member was poured into the female die to a depth of 1 cm, and cured for 2 hours under a condition purged with nitrogen. Further, the liquid material C for producing an ultrasonic propagation member was poured to a depth of 1 cm, and cured for 2 hours under a condition purged with nitrogen, with the male die pressed. Subsequently, the resultant was taken out from the die, to obtain an ultrasonic propagation member.

Example 110

—Preparation of Liquid Material I for Producing Ultrasonic Propagation Member—

First, to pure water (330 parts by mass) under stirring, synthetic hectorite (LAPONITE XLG, available from Rock Wood) having a composition [$Mg_{5.34}Li_{0.66}Si_8O_{20}(OH)_4$] $Na^-_{0.66}$ (16 parts by mass) was added little by little as a water-swellable layered clay mineral, followed by stirring for 3 hours. Next, to the resultant, 1-hydroxyethane-1,1-diphosphonic acid (available from Tokyo Kasei Corporation) (0.6 parts by mass) was added, followed by stirring for 1 hour. Subsequently, to the resultant, glycerin (available from Sakamoto Yakuhin Kogyo Co., Ltd.) (60 parts by mass) was added, followed by stirring for 10 minutes, to produce a dispersion liquid.

Next, to the obtained dispersion liquid, acryloylmorpholine (available from KJ Chemicals Corporation) (16 parts by mass) having been passed through an activated alumina column for removal of a polymerization inhibitor, N,N-dimethyl acrylamide (available from Wako Pure Chemical Industries, Ltd.) (4 parts by mass), and LIGHT ACRYLATE 9EG-A (available from Kyoeisha Chemical Co., Ltd.) (1 part by mass) were added as polymerizable monomers. To the resultant, EMULGEN SLS-106 (available from Kao Corporation) (1 part by mass) was further added as a surfactant and mixed.

Next, to the resultant under cooling in an ice bath, a 4% by mass methanol solution (2.2 parts by mass) of a photopolymerization initiator (IRGACURE 184, available from BASF GmbH) was added, followed by stirring and mixing, and then vacuum degassing for 20 minutes. Subsequently, the resultant was subjected to filtration to remove, for example, impurities, to obtain a liquid material I for producing an ultrasonic propagation member.

—Preparation of Liquid Material J for Producing Ultrasonic Propagation Member—

A liquid material J for producing an ultrasonic propagation member was prepared in the same manner as in preparation of the liquid material I for producing an ultrasonic propagation member, except that the amount of pure water was changed from 330 parts by mass to 1,000 parts by mass unlike in preparation of the liquid material I for producing an ultrasonic propagation member.

—Preparation of Liquid Material for Producing Support—

A liquid material for producing a support was prepared in the same manner as in preparation of the liquid material for producing a support in Example of the first embodiment.

—Production of 3D Ultrasonic Propagation Member—

The liquid material I or J for producing an ultrasonic propagation member and the liquid material for producing a support were filled in two inkjet heads (available from Ricoh Industry Company, Ltd., GEN 4) of an inkjet three-dimensional printer as illustrated in FIG. 9 and discharged, to form films.

CT data of the surface of a breast of a patient (treatment recipient) was converted into data for 3D printing. Based on this data, an ultrasonic propagation member was produced. The liquid material I for producing an ultrasonic propagation member was used first to produce a surface contacting an ultrasonic receiver (the surface having a thickness corresponding to half of the entire ultrasonic propagation member), and the liquid material J for producing an ultrasonic propagation member was used next to produce a surface contacting a human body.

Using an ultraviolet ray irradiator (available from Ushio Inc., SPOT CURE SP5-250DB), the liquid materials I and J for producing an ultrasonic propagation member and the liquid material for producing a support were irradiated and cured with a light volume of 350 mJ/cm$^2$, to produce an ultrasonic propagation member and a support.

After production, the ultrasonic propagation member 17 and the support 18 were drawn in the horizontal direction and separated from each other as illustrated in FIG. 10. As a result, the support 18 was separated as an integrated body, and the ultrasonic propagation member 17 could be easily taken out. In this way, a three-dimensional ultrasonic propagation member for a breast was produced.

Example 111

—Preparation of Liquid Material K for Producing Ultrasonic Propagation Member—

A liquid material K for producing an ultrasonic propagation member was prepared in the same manner as in preparation of the liquid material I for producing an ultrasonic propagation member, except that 0.5 parts by mass out of 1 part by mass of LIGHT ACRYLATE 9EG-A (available from Kyoeisha Chemical Co., Ltd.) was changed to N,N-methylene bisacrylamide (available from Wako Pure Chemical Industries, Ltd.), unlike in preparation of the liquid material I for producing an ultrasonic propagation member.

—Production of 3D Ultrasonic Propagation Member—

A three-dimensional ultrasonic propagation member for a breast was produced in the same manner as in Example 110, except that the liquid material I for producing an ultrasonic propagation member was changed to the liquid material K for producing an ultrasonic propagation member unlike in Example 10.

Example 112

POVAL 205 (available from Kuraray Co., Ltd.) was coated over the surface of the three-dimensional ultrasonic propagation member for a breast produced in Example 110 by a dip coating method, to form a coating film having a thickness of 30 micrometers.

Next, hardness (Young's modulus), transmittance, ultrasonic propagation velocity, and other various properties of each of the three-dimensional ultrasonic propagation members for a breast produced in Example 109 to 112 were evaluated in the same manners as in Example 1. The results are presented in Table 7 and Table 8.

TABLE 7

| | Liquid material for producing ultrasonic propagation member | Coating film | Hardness (Young's modulus) (kPa) Surface contacting human body | Surface contacting ultrasonic receiver | Transmittance (%) | Ultrasonic propagation velocity (m/s) |
|---|---|---|---|---|---|---|
| Ex. 109 | A, C | Absent | 4 | 77 | 81 | 1,565 |
| Ex. 110 | I, J | Absent | 4 | 78 | 81 | 1,540 |
| Ex. 111 | K, J | Absent | 4 | 75 | 81 | 1,540 |
| Ex. 112 | I, J | Present | 4 | 77 | 80 | 1,540 |

TABLE 8

| | Appearance | Dimensions | Elasticity | Heat resistance | Solvent resistance | Close adhesiveness | Post handling | Storage stability |
|---|---|---|---|---|---|---|---|---|
| Ex. 109 | B | B | B | B | B | B | B | B |
| Ex. 110 | B | B | B | B | B | B | B | B |
| Ex. 111 | B | B | A | B | B | B | B | B |
| Ex. 112 | B | B | B | B | B | B | B | A |

(9) Evaluation of Image

Using the three-dimensional ultrasonic propagation members for a breast produced in Examples 109 to 112, image diagnoses were performed using an ultrasonographic instrument. With any of the three-dimensional ultrasonic propagation members for a breast, an image that was clear even at minute portions was obtained.

Aspects of the first embodiment of the present disclosure are, for example, as follows.

<1> An ultrasonic propagation member used in contact with a test target,
wherein a surface of the ultrasonic propagation member contacting the test target has a shape conforming to a surface of the test target.

<2> The ultrasonic propagation member according to <1>, including a hydrogel formed of water, a polymer, and a mineral.

<3> The ultrasonic propagation member according to <1> or <2>,
wherein an ultrasonic propagation velocity in the ultrasonic propagation member is in a range of ±5% from an ultrasonic propagation velocity in water measured at a same temperature.

<4> The ultrasonic propagation member according to any one of <1> to <3>,
wherein hardness of the ultrasonic propagation member expressed by Young's modulus is 0.5 kPa or greater but 100 kPa or less.

<5> The ultrasonic propagation member according to any one of <1> to <4>,
wherein transmittance of the ultrasonic propagation member is 70% or higher.

<6> The ultrasonic propagation member according to any one of <1> to <5>, including
a coating film over a surface of the ultrasonic propagation member.

<7> A method for producing the ultrasonic propagation member according to any one of <1> to <6>, the method including pouring a liquid material for producing an ultrasonic propagation member containing water, a mineral, and a polymerizable monomer into a die produced with a three-dimensional printer based on data of a shape of the surface of the test target, and curing the liquid material to produce the ultrasonic propagation member.

<8> A method for producing the ultrasonic propagation member according to any one of <1> to <6>, the method including producing the ultrasonic propagation member with an inkjet three-dimensional printer configured to discharge a liquid material for producing an ultrasonic propagation member containing water, a mineral, and a polymerizable monomer from an inkjet head based on data of a shape of the surface of the test target and irradiate the liquid material with ultraviolet rays to cure the liquid material.

<9> A method for producing the ultrasonic propagation member according to any one of <1> to <6>, the method including producing the ultrasonic propagation member with a stereolithography three-dimensional printer using a liquid material for producing an ultrasonic propagation member containing water, a mineral, and a polymerizable monomer based on data of a shape of the surface of the test target.

<10> An apparatus configured to produce the ultrasonic propagation member according to any one of <1> to <6>, the apparatus including a discharging unit configured to discharge a liquid material for producing an ultrasonic propagation member containing water, a mineral, and a polymerizable monomer from an inkjet head based on data of a shape of the surface of the test target; and
a curing unit configured to irradiate the liquid material for producing an ultrasonic propagation member discharged with ultraviolet rays to cure the liquid material.

<11> The apparatus configured to produce the ultrasonic propagation member according to <10>,
wherein the apparatus uses an inkjet three-dimensional printer.

The ultrasonic propagation member according to any one of <1> to <6>, the method for producing the ultrasonic propagation member according to any one of <7> to <9>, and the apparatus configured to produce the ultrasonic propagation member according to <10> or <11> can solve the various problems in the related art and achieve the object of the present disclosure.

Aspects of the second embodiment of the present disclosure are, for example, as follows.

<101> An ultrasonic propagation member including at least two surfaces,
wherein hardness of one surface and hardness of another surface are different.

<102> The ultrasonic propagation member according to <101>, wherein the another surface is a surface opposite to the one surface.

<103> The ultrasonic propagation member according to <101> or <102>,
wherein the one surface is a surface contacting an ultrasonic receiver, and the another surface is a surface contacting a test target.

<104> The ultrasonic propagation member according to any one of <101> to <103>,
wherein an ultrasonic propagation velocity in the ultrasonic propagation member is in a range of ±5% from an ultrasonic propagation velocity in water measured at a same temperature.

<105> The ultrasonic propagation member according to <103> or <104>, wherein hardness of the surface contacting an ultrasonic receiver is higher than hardness of the surface contacting a test target.

<106> The ultrasonic propagation member according to any one of <101> to <105>, including
hydrogel formed of water, a polymer, and a mineral.

<107> The ultrasonic propagation member according to any one of <103> to <106>,
wherein hardness of the surface contacting a test target expressed by Young's modulus is 1 kPa or greater but 20 kPa or less.

<108> The ultrasonic propagation member according to any one of <103> to <107>,
wherein hardness of the surface contacting an ultrasonic receiver expressed by Young's modulus is 20 kPa or greater but 100 kPa or less.

<109> The ultrasonic propagation member according to any one of <101> to <108>,
wherein transmittance of the ultrasonic propagation member is 70% or higher.

<110> The ultrasonic propagation member according to any one of <101> to <109>,
wherein a surface of the ultrasonic propagation member contacting a test target has a shape conforming to a surface of the test target.

<111> The ultrasonic propagation member according to any one of <101> to <110>, including
a coating film over a surface of the ultrasonic propagation member.

<112> A method for producing the ultrasonic propagation member according to any one of <101> to <111>, the method including:
producing the ultrasonic propagation member by pouring a liquid material for producing an ultrasonic propagation member into a die produced with a three-dimensional printer based on data of a shape of a surface of a test target, and curing the liquid material, wherein the liquid material contains a water, a mineral, and a polymerizable monomer.

<113> A method for producing the ultrasonic propagation member according to any one of <101> to <111>, the method including:
producing the ultrasonic propagation member with an inkjet three-dimensional printer configured to discharge a liquid material for producing an ultrasonic propagation member from an inkjet head based on data of a shape of a surface of a test target and irradiate the liquid material with ultraviolet rays to cure the liquid material, wherein the liquid material contains water, a mineral, and a polymerizable monomer.

<114> An apparatus configured to produce the ultrasonic propagation member according to any one of <101> to <111>, the apparatus including:
a discharging unit configured to discharge a liquid material for producing an ultrasonic propagation member from an inkjet head based on data of a shape of a surface of a test target, wherein the liquid material contains water, a mineral, and a polymerizable monomer; and
a curing unit configured to irradiate the liquid material for producing an ultrasonic propagation member discharged with ultraviolet rays to cure the liquid material.

<115> The apparatus configured to produce the ultrasonic propagation member according to <114>,
wherein the apparatus uses an inkjet three-dimensional printer.

The ultrasonic propagation member according to any one of <101> to <111>, the method for producing the ultrasonic propagation member according to <112> or <113>, and the apparatus configured to produce the ultrasonic propagation member according to <114> or <115> can solve the various problems in the related art and achieve the object of the present disclosure.

What is claimed is:

1. An ultrasonic propagation member used in contact with a test target,
wherein a surface of the ultrasonic propagation member configured to contact the test target has a shape conforming to a surface of the test target, and
wherein the ultrasonic propagation member is formed of a hydrogel comprising water contained in a three-dimensional network structure formed by a mineral cross-linked and combined with a polymer,
wherein the mineral is a water-swellable layered clay mineral,
wherein the ultrasonic propagation member is produced by curing a liquid material comprising the water, the mineral, a monofunctional monomer, and a multifunctional monomer, wherein the liquid material has a content of monofunctional monomer of 1% by mass or greater but 5% by mass or less relative to the total amount of liquid material and a content of multifunctional monomer of 0.001% by mass or greater but 1% by mass or less relative to the total amount of liquid material,
wherein the ultrasonic propagation member has a content of water of 70% by mass or greater but 95% by mass or less relative to the total amount of the ultrasonic propagation member, and a content of water-swellable layered clay mineral of 1% by mass or greater but 25% by more or less relative to the total amount of ultrasonic propagation member,
wherein the content of monofunctional monomer and water and mineral and multifunctional monomer is such that the hardness of the ultrasonic propagation member expressed by Young's modulus is 0.5 kPa or greater but 100 kPa or less.

2. The ultrasonic propagation member according to claim 1, wherein an ultrasonic propagation velocity in the ultrasonic propagation member is in a range of ±5% from an ultrasonic propagation velocity in water measured at a same temperature.

3. The ultrasonic propagation member according to claim 1, wherein hardness of the ultrasonic propagation member expressed by Young's modulus is 1 kPa or greater but, 50 kPa or less.

4. The ultrasonic propagation member according to claim 1, wherein a transmittance of the ultrasonic propagation member is 70% or higher.

5. The ultrasonic propagation member according to claim 1, further comprising a coating film over a surface of the ultrasonic propagation member.

6. A method for producing the ultrasonic propagation member according to claim 1, the method comprising:
pouring the liquid material for producing the ultrasonic propagation member into a die produced with a three-dimensional printer based on data of a shape of the surface of the test target, and curing the liquid material to produce the ultrasonic propagation member.

7. A method for producing the ultrasonic propagation member according to claim 1, the method comprising:
producing the ultrasonic propagation member with an inkjet three-dimensional printer configured to discharge the liquid material for producing the ultrasonic propagation member from an inkjet head based on data of a shape of the surface of the test target and irradiate the liquid material with ultraviolet rays to cure the liquid material.

8. A method for producing the ultrasonic propagation member according to claim 1, the method comprising:
producing the ultrasonic propagation member with a stereolithography three-dimensional printer using the liquid material for producing an ultrasonic propagation member based on data of a shape of the surface of the test target.

9. The ultrasound propagation member of claim 1, wherein the mineral is a water-swellable hectorite.

10. An ultrasonic propagation member, comprising:
at least two surfaces,
wherein hardness of one surface and hardness of another surface are different;
and
wherein the ultrasonic propagation member is formed of a hydrogel comprising water contained in a three-dimensional network structure formed by a mineral cross-linked and combined with a polymer,
wherein the mineral is a water-swellable layered clay mineral,
wherein the ultrasonic propagation member is produced by curing a liquid material comprising the water, the mineral, a monofunctional monomer, and a multifunctional monomer, wherein the liquid material has a content of monofunctional monomer of 1% by mass or greater but 5% by mass or less relative to the total amount of liquid material and a content of multifunctional monomer of 0.001% by mass or greater but 1% by mass or less relative to the total amount of liquid material, wherein the ultrasonic propagation member has a content of water of 70% by mass or greater but 95% by mass or less relative to the total amount of the ultrasonic propagation member, and a content of water-swellable layered clay mineral of 1% by mass or greater but 25% by more or less relative to the total amount of ultrasonic propagation member, and wherein the content of monofunctional monomer and water and mineral and multifunctional monomer is such that the hardness of the ultrasonic propagation member expressed by Young's modulus is 0.5 kPa or greater but 100 kPa or less.

11. The ultrasonic propagation member according to claim 10, wherein the another surface is a surface opposite to the one surface.

12. The ultrasonic propagation member according to claim 10, wherein the one surface is a surface contacting an ultrasonic receiver, and the another surface is a surface contacting a test target.

13. The ultrasonic propagation member according to claim 10, wherein an ultrasonic propagation velocity in the ultrasonic propagation member is in a range of ±5% from an ultrasonic propagation velocity in water measured at a same temperature.

14. The ultrasonic propagation member according to claim 12, wherein hardness of the surface contacting an ultrasonic receiver is higher than hardness of the surface contacting a test target.

15. The ultrasonic propagation member according to claim 12, wherein hardness of the surface contacting a test target expressed by Young's modulus is 1 kPa or greater but 20 kPa or less.

16. The ultrasonic propagation member according to claim 12, wherein hardness of the surface contacting an ultrasonic receiver expressed by Young's modulus is 20 kPa or greater but 100 kPa or less.

17. The ultrasonic propagation member according to claim 10, wherein a transmittance of the ultrasonic propagation member is 70% or higher.

18. The ultrasonic propagation member according to claim 12, wherein a surface of the ultrasonic propagation member contacting the test target has a shape conforming to a surface of the test target.

19. The ultrasonic propagation member according to claim 10, further comprising a coating film over a surface of the ultrasonic propagation member.

20. The ultrasound propagation member of claim 10, wherein the mineral is a water-swellable hectorite.

* * * * *